United States Patent
Simpson

(10) Patent No.: US 10,716,798 B2
(45) Date of Patent: Jul. 21, 2020

(54) COMPOSITIONS AND METHODS FOR TRANQUILIZING HEART MUSCLE

(75) Inventor: Robert U. Simpson, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 909 days.

(21) Appl. No.: 12/528,246

(22) PCT Filed: Feb. 21, 2008

(86) PCT No.: PCT/US2008/023070
§ 371 (c)(1),
(2), (4) Date: Aug. 21, 2009

(87) PCT Pub. No.: WO2008/103420
PCT Pub. Date: Aug. 28, 2008

(65) Prior Publication Data
US 2009/0325910 A1    Dec. 31, 2009

Related U.S. Application Data

(60) Provisional application No. 60/902,608, filed on Feb. 21, 2007.

(51) Int. Cl.
*A61K 31/59* (2006.01)
*A61K 45/06* (2006.01)

(52) U.S. Cl.
CPC .............. *A61K 31/59* (2013.01); *A61K 45/06* (2013.01)

(58) Field of Classification Search
CPC ..... A61K 31/59; A61K 2300/00; A61K 45/06
USPC ........................................ 514/167; 552/653
See application file for complete search history.

(56) References Cited

U.S. PATENT DOCUMENTS

| 4,391,802 A * | 7/1983 | Suda et al. ................. 514/167 |
| 4,717,721 A | 1/1988 | DeLuca et al. |
| 5,141,927 A * | 8/1992 | Krotkiewski ........ A61K 31/715 514/167 |
| 5,350,745 A * | 9/1994 | Gulbrandsen .......... A61K 31/59 514/167 |

(Continued)

FOREIGN PATENT DOCUMENTS

| WO | WO 2004/019923 | 3/2004 |
| WO | WO-2005097191 A2 | 10/2005 |

OTHER PUBLICATIONS

Levy et al. (JAMA, 1996;275:1557-1562).*

(Continued)

*Primary Examiner* — Sabiha N Qazi
(74) *Attorney, Agent, or Firm* — Harness, Dickey & Pierce, P.L.C.

(57) ABSTRACT

A pharmaceutical composition for tranquilizing cardiomyocytes present in heart muscle in a subject diagnosed with a cardiac overload disease comprises a therapeutically effective amount of a Vitamin $D_5$ compound and a pharmaceutically acceptable excipient. A method for treating or preventing heart failure in a subject diagnosed as having heart failure or being at risk for heart failure, comprises administering to the subject a pharmaceutical composition comprising a therapeutically effective amount of a Vitamin $D_5$ compound and a pharmaceutically acceptable excipient.

14 Claims, 9 Drawing Sheets

(56) References Cited

U.S. PATENT DOCUMENTS

Figure 1:
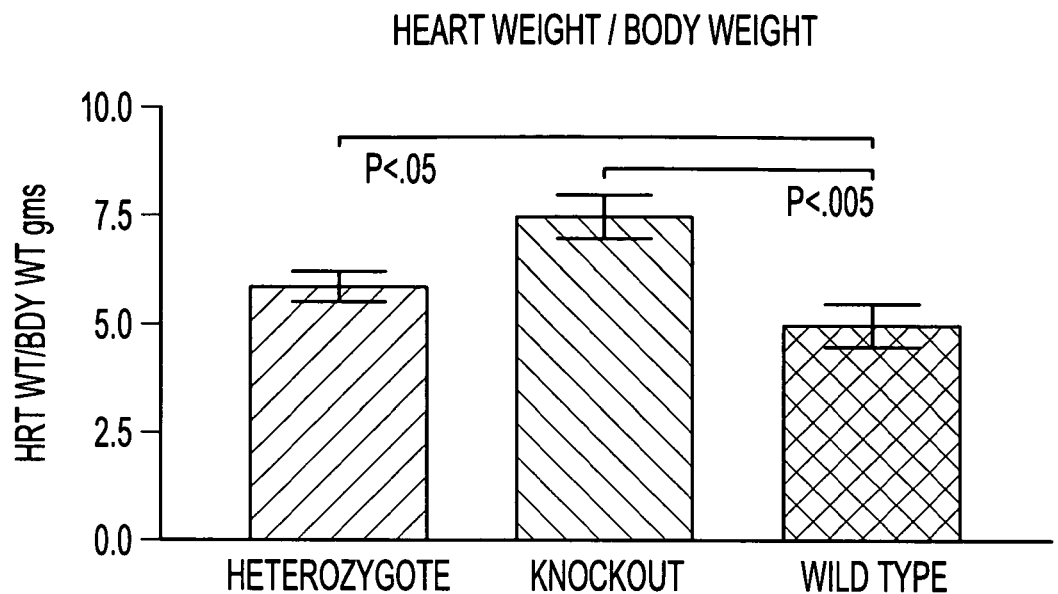

| | | | |
|---|---|---|---|
| 5,700,790 A * | 12/1997 | Gulbrandsen | A61K 31/59 514/167 |
| 6,090,047 A | 7/2000 | Kass et al. | |
| 6,516,294 B1 | 2/2003 | Norman | |
| 6,900,191 B1 * | 5/2005 | Moriarty | C07C 401/00 514/167 |
| 8,168,611 B1 * | 5/2012 | Perrin et al. | 514/52 |
| 8,183,227 B1 * | 5/2012 | Perrin et al. | 514/52 |
| 9,370,527 B2 * | 6/2016 | Simpson | A61K 31/59 |
| 9,517,241 B2 * | 12/2016 | Simpson | A61K 31/59 |
| 2002/0128241 A1 | 9/2002 | Hayes et al. | |
| 2003/0219488 A1 | 11/2003 | Hedden et al. | |
| 2004/0242640 A1 | 12/2004 | Desai et al. | |
| 2005/0074488 A1 * | 4/2005 | Melnick | A61K 9/0019 424/449 |
| 2005/0124591 A1 * | 6/2005 | Tian | A61K 31/401 514/167 |
| 2005/0175691 A1 | 8/2005 | Lee et al. | |
| 2005/0192255 A1 * | 9/2005 | Tian | A61K 31/59 514/167 |
| 2005/0209203 A1 * | 9/2005 | Tian | A61K 31/401 514/167 |
| 2006/0171983 A1 * | 8/2006 | Tian | A61K 31/401 424/422 |
| 2006/0189586 A1 | 8/2006 | Cleland | |
| 2006/0258723 A1 * | 11/2006 | Hamanaka et al. | 514/375 |
| 2007/0037779 A1 * | 2/2007 | Curd et al. | 514/167 |
| 2007/0093459 A1 * | 4/2007 | Tian | A61K 31/401 514/167 |

OTHER PUBLICATIONS

Vieth et al. (Am J Clin. Nutr 2006; 83:731-2).*
Right fax.*
Lemmila et al. (Am J Nephrol. 1998; 18(5):404-10).*
McGonigle et al. (Proc Eur Dial Transplant Assoc. 1981; 18:579-85).*
Napoli et al. (abstract Archives of Biochemistry and Biophysics, vol. 197, Issue 1, |Oct. 1979, pp. 119-125).*
Joseph L. Napoli et al. (Archives of Biochemistry and Biophysics, vol. 197, No. 1, Oct. 1, pp. 119-125, 1979).*
Erum A.Hussain-Hakimjee et al. (Carcinogenesis, vol. 27, No. 3, pp. 551-559, 2006).*
Timothy D. O'Connell et al. (Am. J. Physiol. 272 (Heart Circ. Physiol. 41): H1751-1758, 1997).*
Mehta et al. (Journal of Nutritional Biochemistry 13 (.2002) 252-264).*
Mehta et al. (Journal of National cancer Institute, vol. 89, No. 3, Feb. 5, 1997).*
Walters et al. (Calcified Tissue International, Dec. 1983, vol. 35, Issue 1, pp. 372-375; Studies on the mode of action of vitamin D XXXVII 1α-hydroxyvitamin D3: A long-acting 1,25-dihydroxyvitamin D3 analog).*
Supplementary European Search Report dated Dec. 16, 2010 (3 pgs.).
Office Action regarding European Patent Application No. 08725897.6, dated Jul. 13, 2012.
Bella et al., "Mitral Ratio of Peak Early to Late Diastolic Filling Velocity as a Predictor of Mortality in Middle-Aged and Elderly Adults: The Strong Heart Study." Circulation, vol. 105, No. 16, pp. 1928-1933 (2002).
Buitrago et al., "Nongenomic action of 1α,25(OH)$_2$-vitamin D$_3$: Activation of muscle cell PLCγ through the tyrosine kinase c-Src and Ptdlns 3-kinase." European Journal of Biochemistry, vol. 269, No. 10, pp. 2506-2515 (2002).
Casale et al., "Improved sex-specific criteria of left ventricular hypertrophy for clinical and computer interpretation of electrocardiograms: validation with autopsy findings." Circulation, vol. 75, No. 3, pp. 565-572 (1987).
Cokkinos et al., "Efficacy of antithrombotic therapy in chronic heart failure: The HELAS study." The European Journal of Heart Failure, vol. 8, No. 4, pp. 428-432 (2006).
de Zeeuw et al., "Selective vitamin D receptor activation with paricalcitol for reduction of albuminuria in patients with type 2 diabetes (VITAL study): a randomised controlled trial." Lancet, vol. 376, No. 9752, pp. 1543-1551 (2010).
Factor et al., "Clinical and morphological features of human hypertensive-diabetic cardiomyopathy." American Heart Journal, vol. 99, No. 4, pp. 446-458 (1980).
Factor et al., "Hypertensive diabetic cardiomyopathy in the rat: ultrastructural features." Virchows Archiv: European Journal of Pathology, vol. 398, No. 3, pp. 305-317 (1983).
Green et al., "Calcitriol modulation of cardiac contractile performance via protein kinase C." Journal of Molecular and Cellular Cardiology, vol. 41, No. 2, pp. 350-359 (2006).
Heyen et al., "Structural, functional, and molecular characterization of the SHHF model of heart failure." American Journal of Physiology—Heart and Circulatory Physiology, vol. 283, No. 5, pp. H1775-H1784 (2002).
Jones et al., "Hepatic Activation and Inactivation of Clinically-relevant Vitamin D Analogs and Prodrugs," Anticancer Research, vol. 26, No. 4A, pp. 2589-2595 (2006).
Kass et al., "From 'Emax' to pressure-volume relations: a broader view." Circulation, vol. 77, No. 6, pp. 1203-1212 (1988).
Kass et al., "Use of a Conductance (Volume) Catheter and Transient Inferior Vena Caval Occlusion for Rapid Determination of Pressure-Volume Relationships in Man." Catheterization and Cardiovascular Diagnosis, vol. 15, No. 3, pp. 192-202 (1988).
Levy et al., "Determinants of sensitivity and specificity of electrocardiographic criteria for left ventricular hypertrophy." Circulation, vol. 81, No. 3, pp. 815-820 (1990).
Li et al., "1,25-dihydroxyvitamin D$_3$ inhibits renal interstitial myofibroblast activation by inducing hepatocyte growth factor expression." Kidney International, vol. 68, No. 4, pp. 1500-1510 (2005).
Mayet et al., "Cardiac and vascular pathophysiology in hypertension." Heart, vol. 89, No. 9, pp. 1104-1109 (2003).
O'Connell et al., "Immunochemical identification of the 1,25-dihydroxyvitamin D$_3$ receptor protein in human heart" Cell Biology International, vol. 20, No. 9, pp. 621-624 (1996).
Ohsawa et al., "1α,25-Dihydroxyvitamin D$_3$ and Its Potent Synthetic Analogs Downregulate Tissue Factor and Upregulate Thrombomodulin Expression in Monocytic Cells, Counteracting the Effects of Tumor Necrosis Factor and Oxidized LDL." Circulation, vol. 102, No. 23, pp. 2867-2872 (2000).
Pedrozo et al., "Physiological Importance of the 1,25(OH)$_2$D$_3$ Membrane Receptor and Evidence for a Membrane Receptor Specific for 24.25(OH)$_2$D$_3$." Journal of Bone and Mineral Research, vol. 14, No. 6, pp. 856-867 (1999).
Romhilt et al., "A point-score system for the ECG diagnosis of left ventricular hypertrophy." American Heart Journal, vol. 75, No. 6, pp. 752-758 (1968).
Senzaki et al., "Single-Beat Estimation of End-Systolic Pressure-Volume Relation in Humans." Circulation, vol. 94, No. 10, pp. 2497-2506 (1996).
Shen et al., "Prognostic significance of Doppler-derived left ventricular diastolic filling variables in dilated cartliomyopathy." American Heart Journal, vol. 124, No. 6, pp. 1524-1533 (1992).
Simpson et al., "Characterization of heart size and blood pressure in the vitamin D receptor knockout mouse." Journal of Steroid Biochemistry & Molecular Biology, vol. 103, No. 3-5, pp. 521-524 (2007).
Simpson et al., "Identification of 1,25-Dihydroxyvitamin D3 Receptors and Activities in Muscle." The Journal of Biological Chemistry, vol. 260, No. 15, pp. 8882-8891 (1985).
Simpson et al., "Newly Discovered Activities for Calcitriol (1,25-Dihydroxyvitamin D$_3$): Implications for Future Pharmacological Use." BioEssays, vol. 4, No. 2, pp. 65-70 (1986).
Sokolow et al., "The ventricular complex in left ventricular hypertrophy as obtained by unipolar precordial and limb leads." American Heart Journal, vol. 37, No. 2, pp. 161-186 (1949).

(56) References Cited

OTHER PUBLICATIONS

Sunagawa et al., "Estimation of the hydromotive source pressure from ejecting beats of the left ventricle." IEEE Transactions on Biomedical Engineering, vol. 27, No. 6, pp. 299-305 (1980).
Unverferth et al., "Extent of myocardial fibrosis and cellular hypertrophy in dilated cardiomyopathy." The American Journal of Cardiology, vol. 57, No. 10, pp. 816-820 (1986).
Walters et al., "1,25-Dihydroxyvitamin $D_3$ receptors identified in the rat heart." Journal of Molecular and Cellular Cardiology, vol. 18, No. 1, pp. 67-72 (1986).
Weishaar et al., "Involvement of vitamin $D_3$ with cardiovascular function. II. Direct and indirect effects." American Journal of Physiology—Endocrinology and Metabolism, vol. 253, No. 6, pp. E675-E683 (1987).
Willette et al., "In Vitro and In Vivo Characterization of Intrinsic Sympathomimetic Activity in Normal and Heart Failure Rats." The Journal of Pharmacology and Experimental Therapeutics, vol. 289, No. 1, pp. 48-53 (1999).
Xiang et al., "Cardiac hypertrophy in vitamin D receptor knockout mice: role of the systemic and cardiac renin-angiotensin systems." American Journal of Physiology—Endocrinology and Metabolism, vol. 288, No. 1, pp. E125-E132 (2005).
Yen et al., "A Genetic Study of Hypertension in Okamoto-Aoki Spontaneously Hypertensive Rats." Heredity, vol. 33, No. 3, pp. 309-316 (1974).
Zittermann et al., "Low vitamin D status: a contributing factor in the pathogenesis of congestive heart failure?" Journal of the American College of Cardiology, vol. 41, No. 1, pp. 105-112 (2003).

\* cited by examiner

COMPOSITIONS AND METHODS FOR TRANQUILIZING HEART MUSCLE

CROSS-REFERENCE TO RELATED APPLICATIONS

This application is the U.S. National Phase Application under 35 U.S.C. 371 of International Application No. PCT/US2008/002307 filed on Feb. 21, 2008, which claims the benefit of U.S. Provisional Application No. 60/902,608 filed on Feb. 21, 2007. The disclosures of the above applications are incorporated herein by reference.

GOVERNMENT RIGHTS

This disclosure was made with government support under National Institutes of Health Grant Nos. HL-067254 and HL-074894. The Government has certain rights in the invention.

FIELD

The present disclosure relates to compositions and methods for tranquilizing cardiac myocytes. More particularly, the present disclosure relates to the use of Vitamin $D_5$ compounds, to tranquilize the heart as a treatment for cardiac related diseases, especially cardiac hypertrophy, heart failure, congestive heart failure, cardiomyopathy, arrhythmias, angina, myocardial infarction, hypertension and coronary artery disease.

BACKGROUND

The statements in this section merely provide background information related to the present disclosure and may not constitute prior art.

Several lines of evidence suggest that Vitamin D plays a crucial role in myocardial function and metabolism. Studies performed in animals and cell culture have shown that Vitamin $D_3$ and $D_5$ and in particular the metabolically active form $1\alpha25(OH)_2D_3$ exerts direct effects on heart skeletal muscle $Ca^{2+}$ metabolism, contractility and growth. Butriago, C., et al. Eur. J. Biochem. 269:2506-2515 (2002). Moreover, such effects were shown to be mediated through specific Vitamin D receptors (VDR). Simpson, R. U., et al. J. Biol. Chem. 260(15): 8882-8891. Biological activity of $1\alpha25(OH)_2D_3$ has been shown to proceed through two distinct pathways. The first characterized pathway involves signal mediated through nuclear Vitamin D receptor gene transcription. The second, more recently studied activity involves a rapid, non-genomic pathway that occurs within 30 minutes and is not reliant on RNA and protein synthesis. The exact non-genomic pathway involving Vitamin $D_3$ in muscle and epithelial cells has not been exactly elucidated and is presently being extensively studied.

Several cardiac diseases are associated with dysfunctional cardiomyocyte structure and function. Two important conditions related to an improperly functioning heart include heart failure (HF) or cardiac hypertrophy and arrhythmias. HF is a leading cause of mortality in industrialized nations. Most patients with HF have a history of hypertension and/or left ventricular hypertrophy (LVH), and as a result these diseases are intimately linked. During the initial and middle stages of HF, the heart responds acutely to increased demand or overload by increasing the stroke volume and heart rate, which can raise cardiac output significantly over basal levels. Prolonged overload leads to cardiac remodeling which includes hypertrophy, loss of myocytes and increased interstitial fibrosis. Initially, these are adaptive changes which allow some normalized function by increasing the pumping capacity of the heart. Eventually, however, these compensatory mechanisms lead to reduced cardiac function and pathological symptoms become evident especially if the supply of oxygen or nutrients to the heart muscle is compromised. Increased muscle cell mass raises oxygen consumption and therefore predisposes the hypertrophic heart to ischemia. Furthermore, the heart is more susceptible to arrythmias, cardiac infarction, angina, chronic renal failure and ischemic and non-ischemic cardiomyopathy. The degree of remodeling progressively increases resulting in increased connective tissue formation concurrent with increasing cell mass, causing cardiac fibrosis. The increased stiffness of the left ventricular wall directly leads to diastolic HF.

Several other cardiac related conditions can manifest as a result of poor cardiac function due to cardiac overload and LVH including: arrythmias, cardiac infarction, angina, myocardial ischemia and cardiomyopathy. Despite studies and treatments for HF targeting the neurohormonal system and its cognate factors implicated in HF, there is a great need to understand the biology of the dysfunction and dysregulation of the cardiac myocyte itself. Many of these neurohormonal system factors have specific roles outside of the contractile cardiac myocyte itself, such as regulation of blood pressure and sodium retention, conditions that may affect the remodeling of the cardiomyocyte itself, albeit somewhat indirectly.

All of these findings demonstrate the importance of Vitamin D in progression of cardiac overload and the resultant diseases therefrom. The non-genomic pathway presents a convergence point for modulating cardiac output and cell contractility. To date, the exact pathways for regulating cardiomyocyte contraction via Vitamin D receptors have not been fully identified.

Gulbrandsen et al. (U.S. Pat. No. 5,700,790) reports a method for preventing myocardial failure in a mammal by administering an activated Vitamin D compound to produce a positive inotropic effect in the heart muscle. The vitamin D compounds used in Gulbrandsen et al. include, $1\alpha$-hydroxylated vitamin $D_2$, $D_3$ and $D_4$ compounds. Gulbrandsen et al. rely on the ability of these Vitamin D compounds to increase the strength of the heart's contraction. However, the patent fails to show whether the administration of any Vitamin D compound changes the hemodynamic properties of any mammalian heart in vivo, including hearts that are under cardiac overload or hemodynamic stress, such as in a HF or a hypertensive subject. Moreover, Gulbrandsen et al. fails to describe methods for preventing the sequence of processes associated with the stages of compensatory heart failure morbidity that ultimately lead to decompensated heart failure mortality.

The present disclosure provides herein, the use of Vitamin $D_5$ analogs acting upon Vitamin D receptors in the cardiomyocyte membrane and/or nucleus to relax the cardiomyocyte and thus ameliorate and prevent the remodeling process normally seen in cardiac overload diseases as a result of increased cardiac demand. As such, novel Vitamin $D_5$ therapies and pharmaceutical compositions comprising Vitamin $D_5$ compounds represent an excellent therapeutic avenue for treating cardiac overload and its related pathologies by directly treating the cardiomyocyte itself.

SUMMARY

The present disclosure provides for a pharmaceutical composition for tranquilizing cardiomyocytes present in heart muscle in a subject diagnosed with a cardiac overload disease comprising a therapeutically effective amount of a Vitamin $D_5$ compound and a pharmaceutically acceptable excipient. In some embodiments, the Vitamin $D_5$ compound is 1α-hydroxysitocalciferol.

In another aspect, the present disclosure provides for a pharmaceutical composition for tranquilizing cardiomyocytes present in heart muscle in a subject associated with a cardiac overload disease comprising a therapeutically effective dose of Vitamin $D_5$, a pharmaceutically acceptable excipient and a cardiac muscle relaxant wherein the cardiac muscle relaxant is a beta-adrenergic receptor blocker, an anti-hypertensive agent, an anti-arrythmia agent, 2,3-butanedione monoxime or combinations thereof.

There is further provided a method for tranquilizing the heart of a subject with a cardiac overload disease, the method comprising providing pharmaceutical composition comprising a Vitamin $D_5$ compound and at least one pharmaceutically acceptable excipient; and administering an effective amount of the composition to the subject.

In some embodiments, the cardiac overload disease can include any one or more of heart failure, left ventricular hypertrophy, decompensated heart failure, ischemic cardiomyopathy, dilated cardiomyopathy, myocardial ischemia, atherosclerosis, coronary artery disease, angina pectoris, myocardial infarction, hypertension, cardiac arrythmia and chronic renal failure.

There is still further provided a method for treating or preventing heart failure in a subject diagnosed as having heart failure or being at risk for heart failure, the method comprising the step of administering to the subject, a pharmaceutical composition comprising a therapeutically effective amount of a Vitamin $D_5$ compound and a pharmaceutically acceptable excipient. In some embodiments the method also comprises administering a composition comprising a Vitamin $D_5$ compound, a pharmaceutically acceptable excipient and a cardiac muscle relaxant wherein the cardiac muscle relaxant is a beta-adrenergic receptor blocker, an anti-hypertensive agent, an anti-arrythmia agent, 2,3-butanedione monoxime or combinations thereof.

There is still further provided a method for reducing at least one of cardiac index, stroke volume and E/A ratio in a subject diagnosed as having at least one of cardiac hypertrophy and heart failure or at risk for developing cardiac hypertrophy and heart failure, the method comprising the step of administering to the subject, a pharmaceutical composition comprising a Vitamin $D_5$ compound and a pharmaceutically acceptable excipient.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1. depicts heart weight/body weight ratios (×1000) for VDR heterozygous [(+/−) n=6], knockout [(−/−) n=6] and wild type [(+/+) n=5] mice. Mice were bred from mothers maintained on a diet containing 2% calcium, 1.25% phosphate and 20% lactose (Teklad #96348) and remained on this diet for 12 months in accordance to the methods of the present disclosure.

Figure 2:
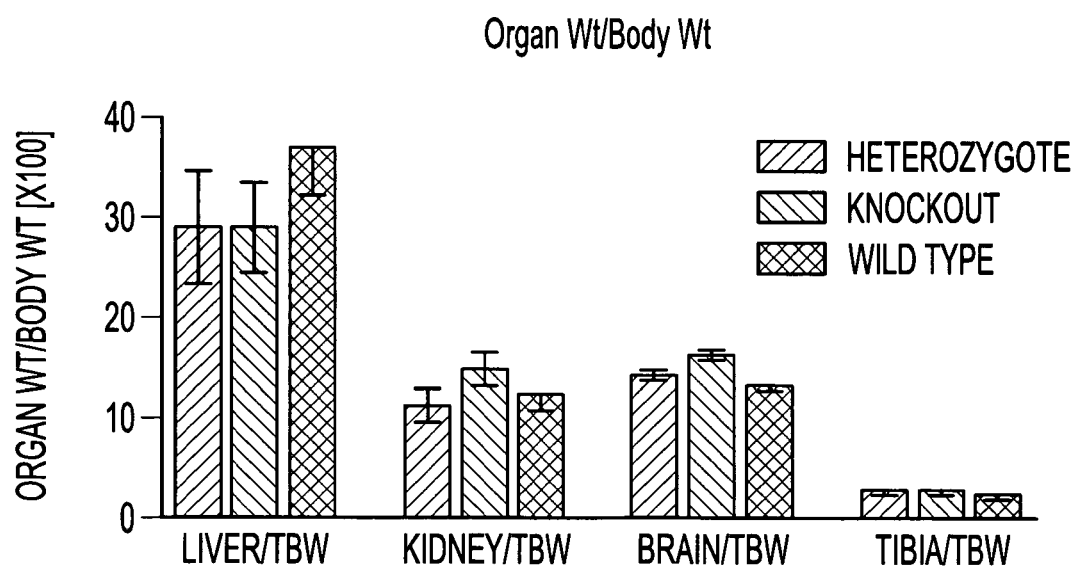

FIG. 2. depicts organ weight/body weight ratios (×1000) are for VDR heterozygous [(+/−) n=6], knockout [(−/−) n=6] and wild type [(+/+) n=5] mice. Body weight were: (+/−)=30.7±4.9 g; (−/−)=27.7±4.8 g and (+/+)=34.3±5.9 [X+S.D.]. Liver, kidney, brain and tibia were removed, dried, cleaned of other tissues and weighed from the 12-month-old mice in accordance to the methods of the present disclosure.

Figure 3:
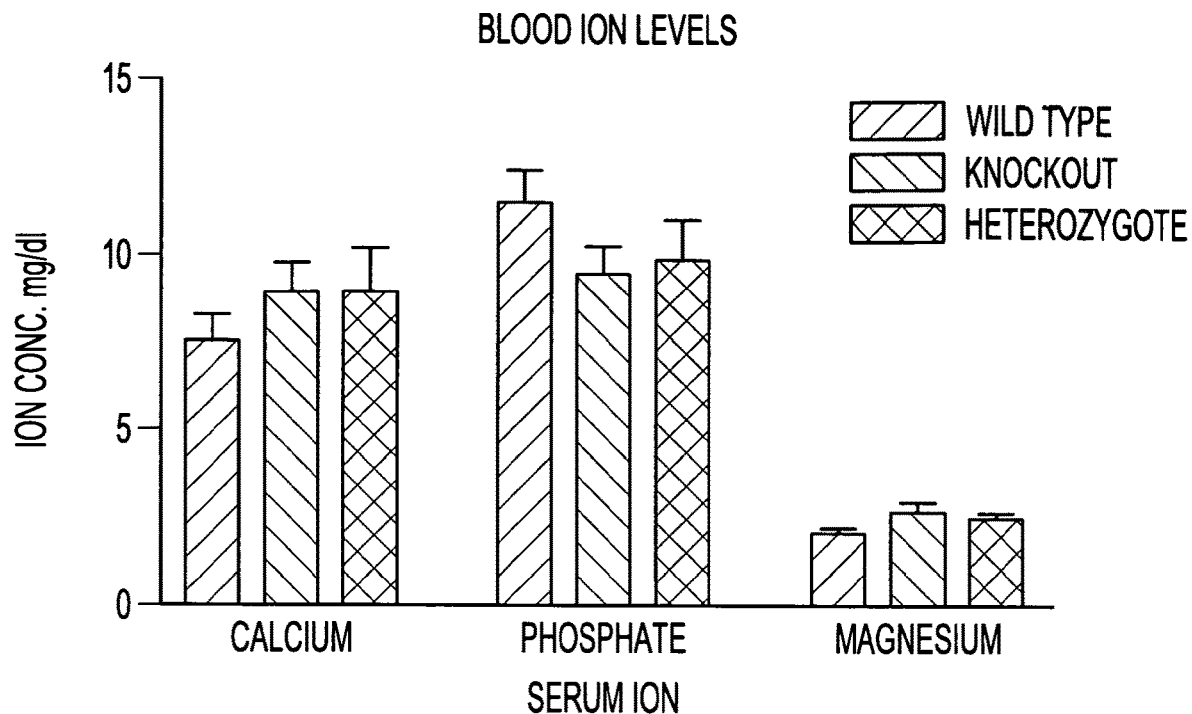

FIG. 3. depicts blood ion levels from the 12 month old mice maintained on the 2% calcium, 1.25% phosphate and 20% lactose diet. Veinous blood was obtained from the inferior vena cava and plasma analyzed for total calcium, phosphate and magnesium in accordance to the methods of the present disclosure.

Figure 4:
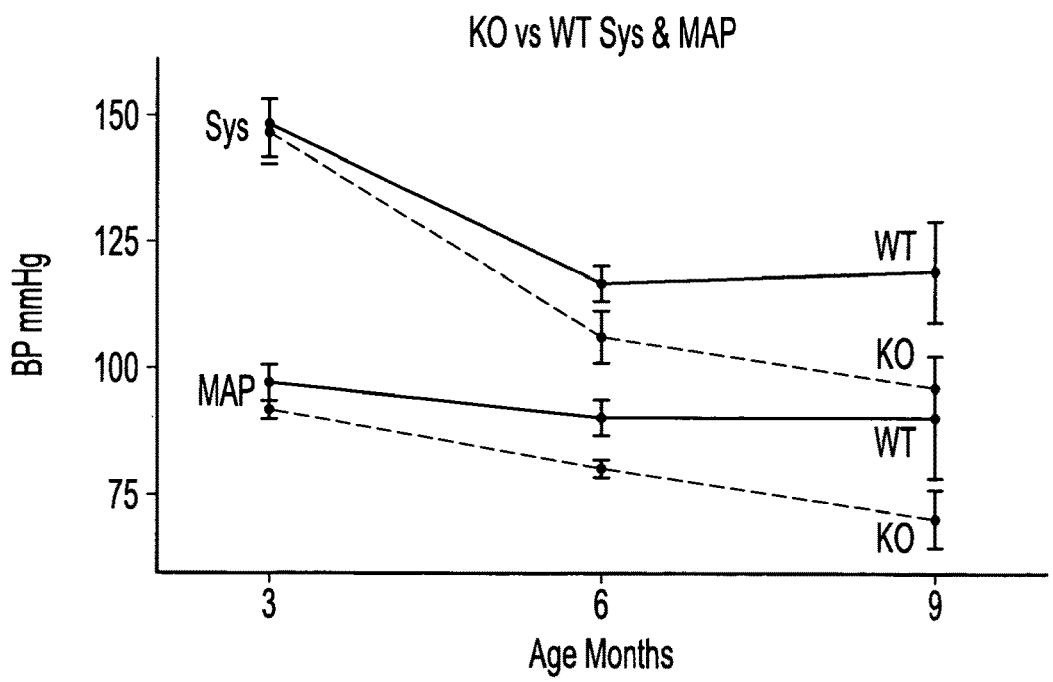

FIG. 4. depicts age-dependant and phenotype dependant changes in systolic blood pressure and calculated mean arterial blood pressure of knockout (open circles) and wild type (closed circles) mice on the high calcium diet. Non-invasive blood pressures were measured by tail cuff occlusion using an eMouse Specifics Inc. apparatus. Ten measurements were taken for each mouse at each time point and averaged. The group average was then calculated and data presented as mean±standard deviation in accordance to the methods of the present disclosure.

Figure 5:
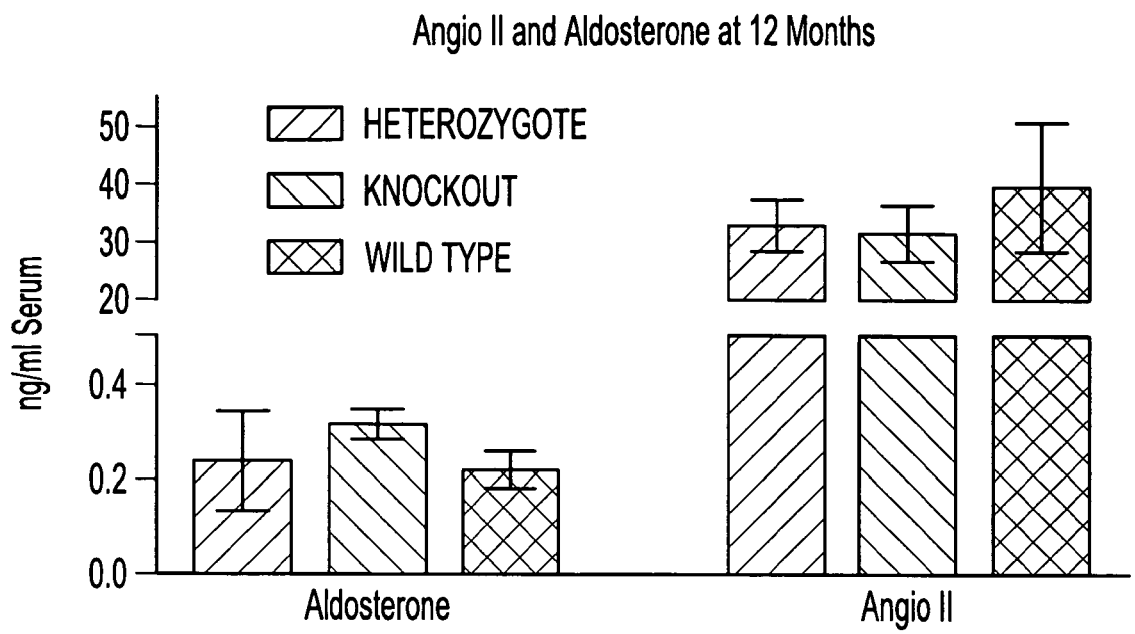

FIG. 5. depicts blood angiotensin II and aldosterone levels were measured by radioimmunoassay methods. n=6 for heterozygous, n=5 for wild type and n=6 for knockout mice. Data displayed as mean±standard deviation in accordance to the methods of the present disclosure.

Figure 6:
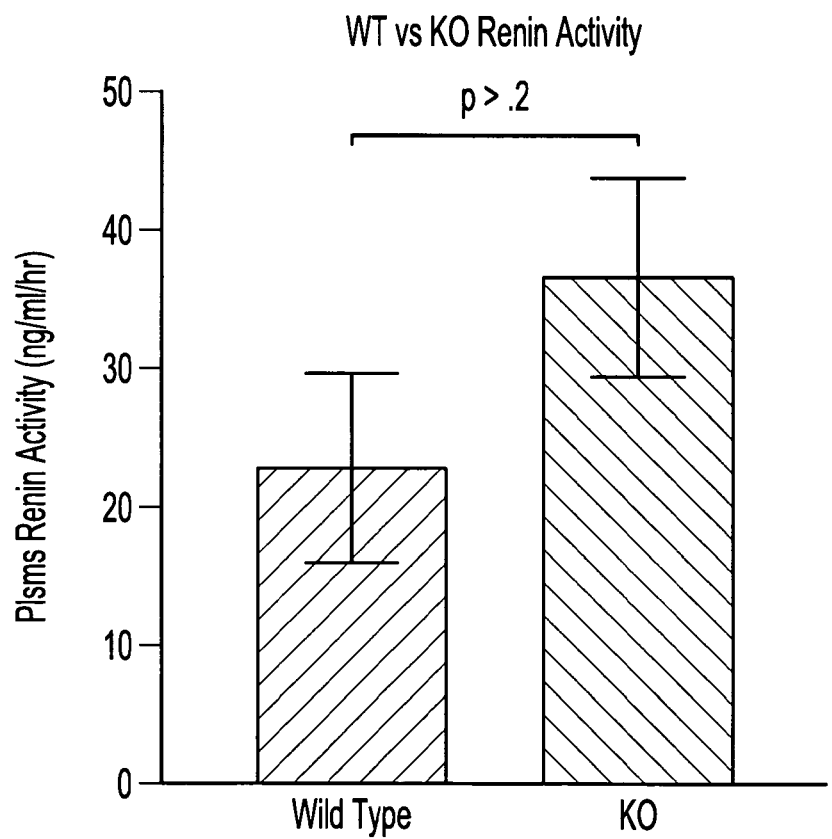

FIG. 6. depicts plasma renin activity. Mouse plasma pooled sample with n=3 for knockout and n=3 wild type mice in accordance to the methods of the present disclosure. No significance differences were observed P>0.02.

Figure 7:
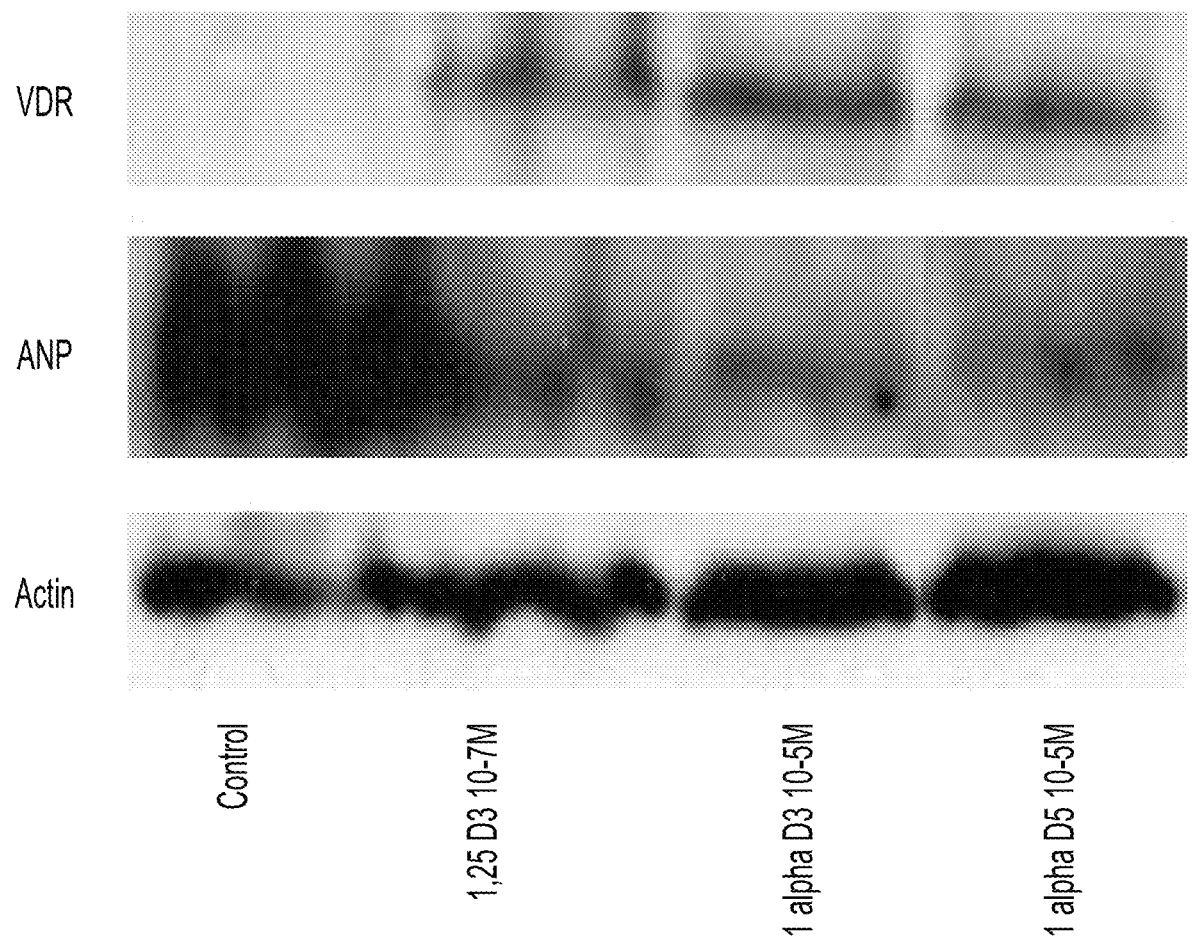

FIG. 7 depicts an electropherogram of induction of Vitamin D receptor and the production of atrial natriuretic peptide (ANP) in HL-1 Cardiomyocytes in the presence and absence of Vitamin $D_3$ and Vitamin $D_5$.

Figure 8:
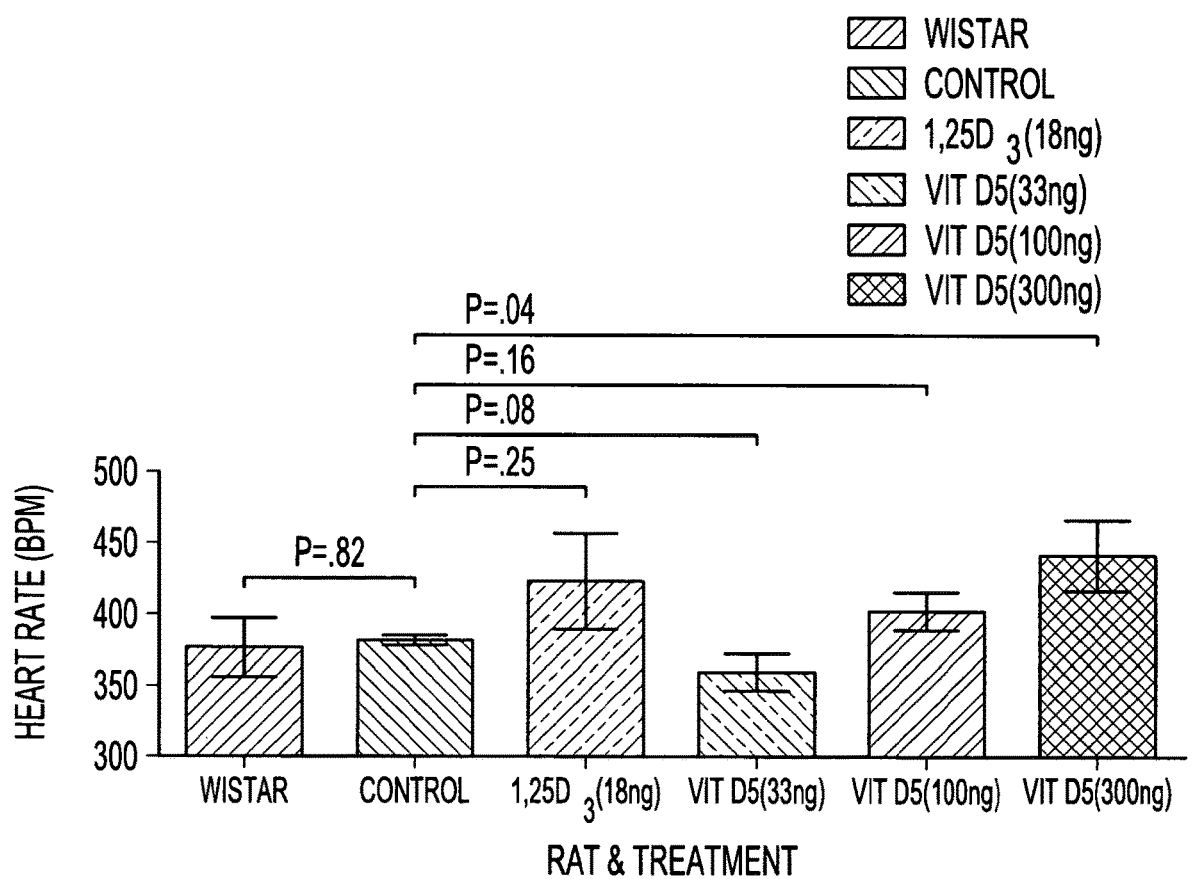

FIG. 8 depicts a graphical representation of heart rate in beats per minute (bpm) for Wistar-Furth rats (a non-hypertensive control group; N=6) and SHHF rats (N=6/group) treated with vehicle, 1,25(OH)$_2$D$_3$ (18 ng/100 g body weight), or 1α-hydroxysitocalciferol at 33, 100 or 300 ng/100 g body weight. Student t-test (2 tail) revealed no differences except at 300 ng 1α-hydroxysitocalciferol and a decrease (1 tail: P=0.04) bpm at 33 ng 1α-hydroxysitocalciferol. The 18 ng 1,25(OH)$_2$D$_3$ and 300 ng 1α-hydroxysitocalciferol heart rates are similar.

Figure 9:
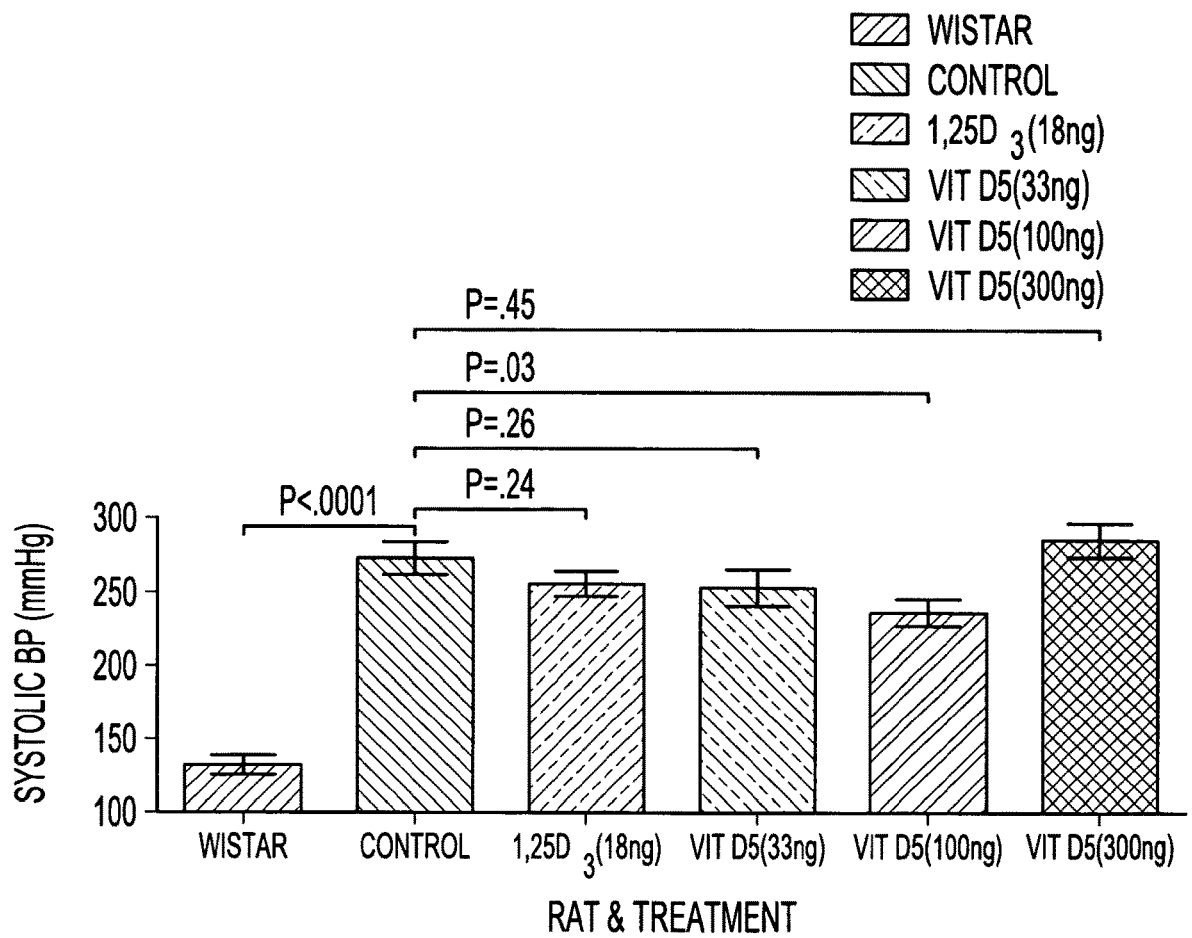

FIG. 9 depicts graphical representation of systolic blood pressure (BP) in mmHg for Wistar-Furth rats (a non-hypertensive control group; N=6) and SHHF rats (N=6/group) treated with vehicle, 1,25(OH)$_2$D$_3$ (18 ng/100 g bw), or 1α-hydroxysitocalciferol (33, 100 or 300 ng/100 g bw). Student t-test (2 tail) revealed large BP increase in untreated SHHF controls versus Wistar rats and a significant decreased BP for 100 ng 1α-hydroxysitocalciferol (2 tail: P=0.03) treated SHHF rats versus control SHHF rats.

Figure 10:
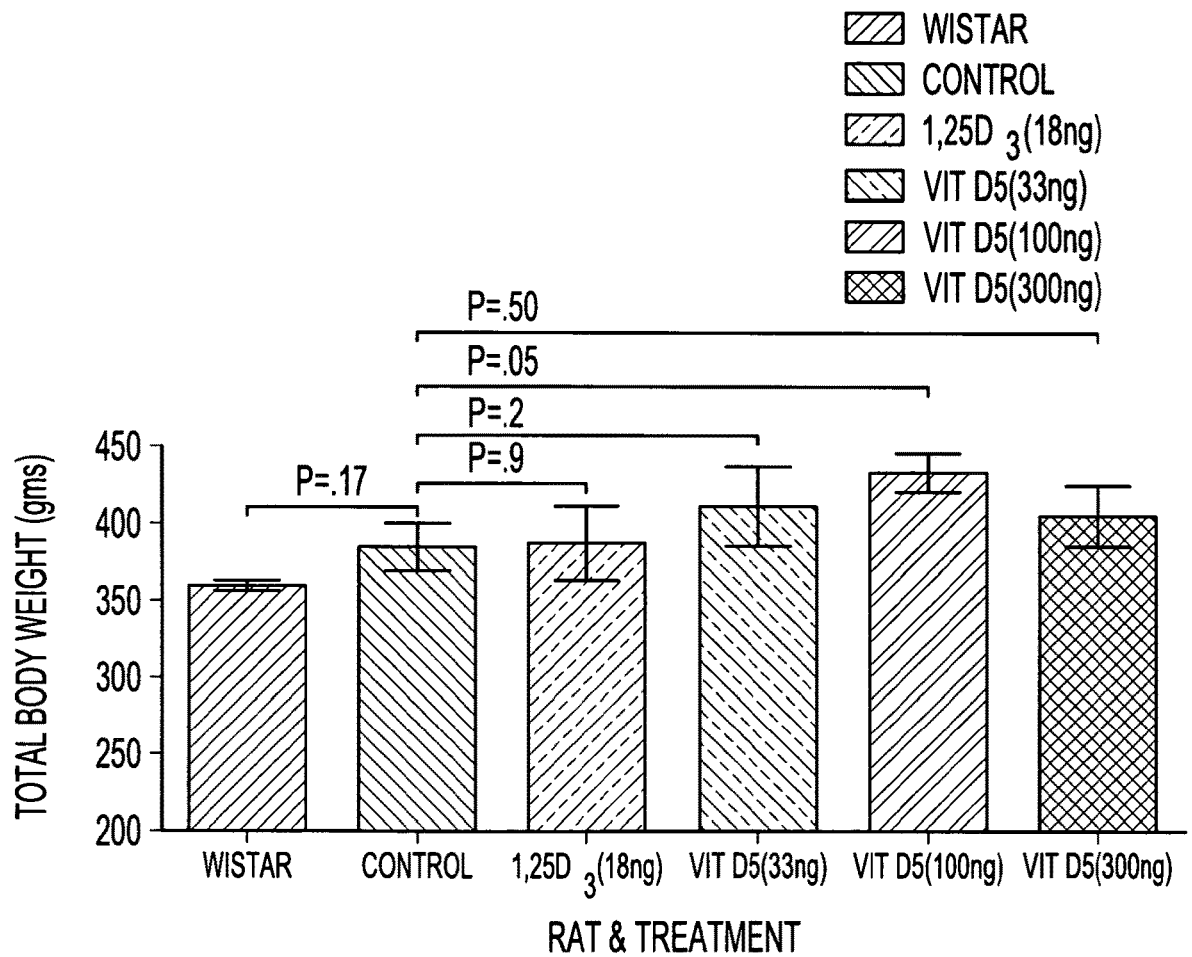

FIG. 10 depicts graphical representation of total body weight at 30 weeks age for Wistar-Furth rats (a non-hypertensive control group; N=6) and SHHF rats (N=6/group) treated with vehicle, 1,25(OH)$_2$D$_3$ (18 ng/100 g body weight), or 1α-hydroxysitocalciferol (33, 100 or 300 ng/100 g body weight). Student t-test (2 tail) revealed no increase in total body weight for untreated SHHF controls versus Wistar rats and a significant increased body weight for 100 ng 1α-hydroxysitocalciferol (2 tail: P=0.03) treated SHHF rats versus control SHHF rats.

Figure 11:
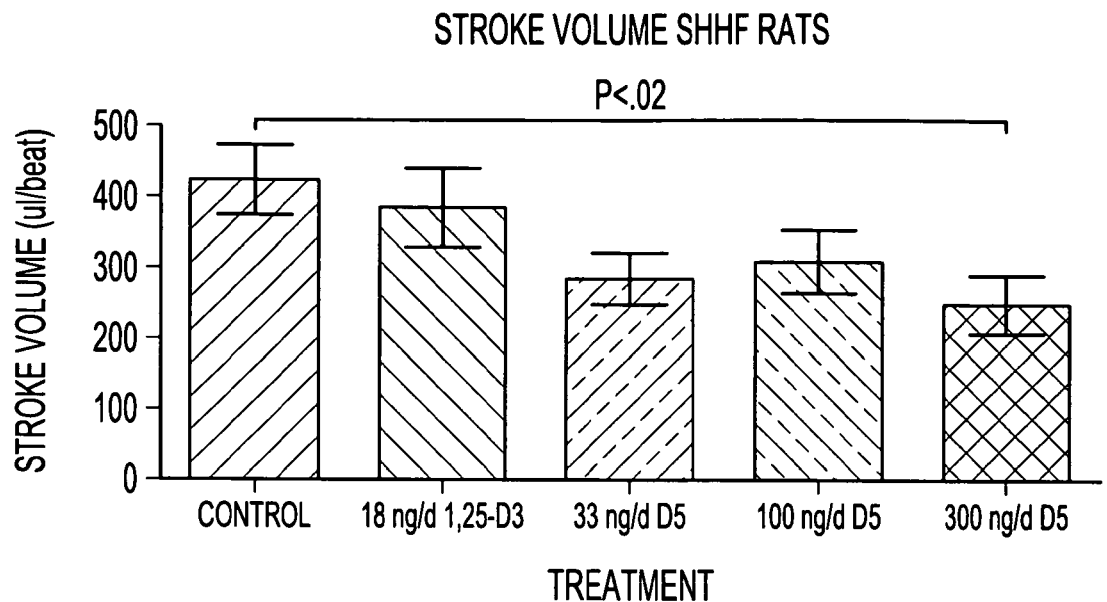

FIG. 11 depicts a graphical representation of the stroke volume in SHHF treated and untreated rats. The stroke volume is represented as microliters blood per heart beat. Rats (N=6) were grouped as control (vehicle alone), 18 ng/day of 1,25(OH)$_2$D$_3$, 33, 100 and 300 ng/day 1α-hydroxysitocalciferol. Treatments were administered 5 days per week for 13 weeks. Upon the 13 week completion, the stroke volume was determined using electrocardiography in accordance with the present disclosure. Student t-test (2 tail) revealed a statistically significant reduction in stroke volume of the 300 ng/day 1α-hydroxysitocalciferol treated SHHF rats compared to control.

Figure 12:
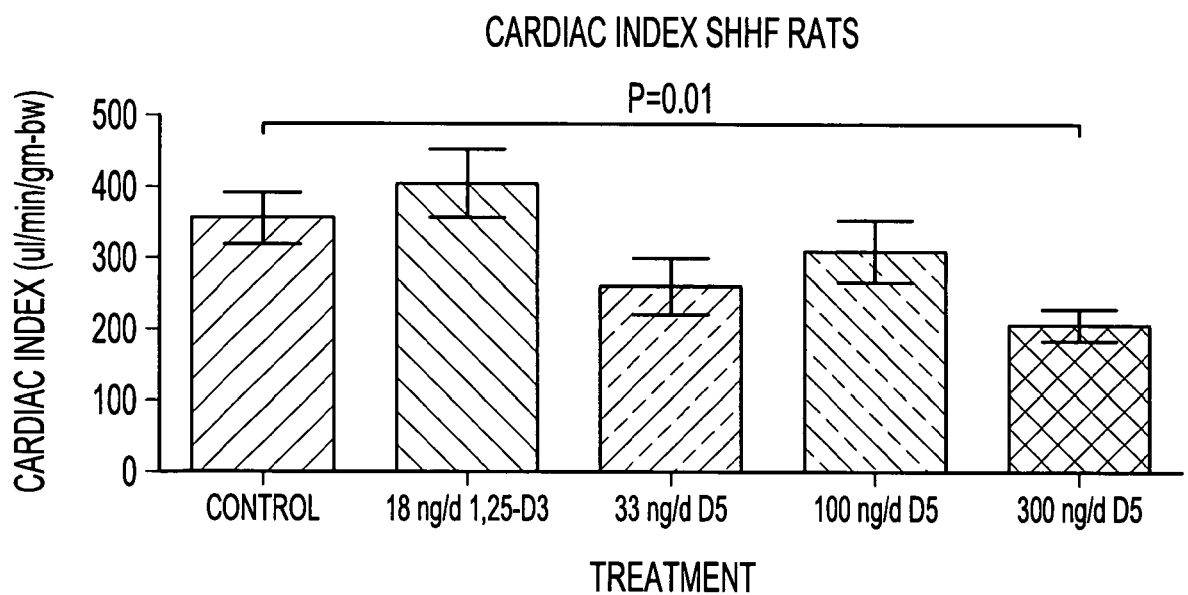

FIG. 12 depicts a graphical representation of the cardiac index in SHHF treated and untreated rats. The cardiac index is represented as microliters blood per minute per weight (grams). Rats (N=6) were grouped as control (vehicle alone), 18 ng/day of 1,25(OH)$_2$D$_3$, 33, 100 and 300 ng/day 1α-hydroxysitocalciferol. Treatments were administered 5 days per week for 13 weeks. Upon the 13 week completion, the cardiac index was determined using electrocardiography in accordance with the present disclosure. Student t-test (2 tail) revealed a statistically significant reduction in cardiac index of the 300 ng/day 1α-hydroxysitocalciferol treated SHHF rats compared to control.

Figure 13:
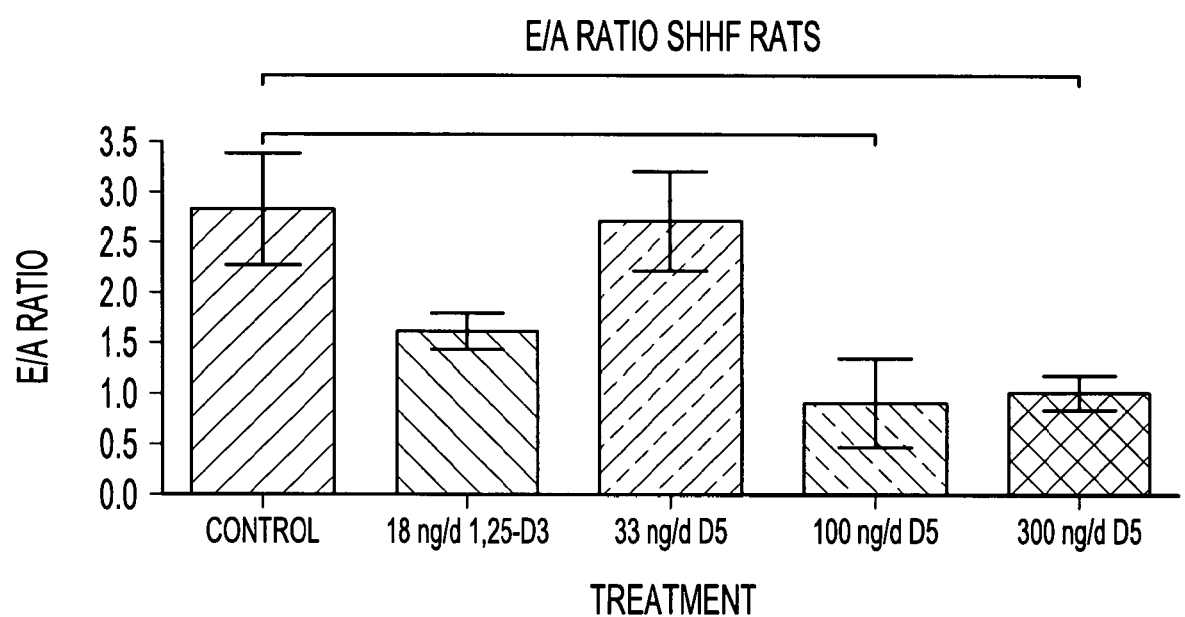

FIG. 13 depicts a graphical representation of the E/A transmitral flow ratio in SHHF treated and untreated rats. Rats (N=6) were grouped as control (vehicle alone), 18 ng/day of 1,25(OH)$_2$D$_3$, 33, 100 and 300 ng/day 1α-hydroxysitocalciferol. Treatments were administered 5 days per week for 13 weeks. Upon the 13 week completion, the E/A ratio was determined using electrocardiography in accordance with the present disclosure. Student t-test (2 tail) revealed a statistically significant reduction in the E/A ratio of the 100 and 300 ng/day 1α-hydroxysitocalciferol treated SHHF rats (within normal values) compared to control (E/A ratio indicative of heart failure).

DETAILED DESCRIPTION

The following description is merely exemplary in nature and is not intended to limit the present disclosure, application, or uses.

The present disclosure provides pharmaceutical compositions including a Vitamin D$_5$ compound and a pharmaceutically acceptable excipient or carrier. The present disclosure also provides methods for treating cardiac overload diseases or disorders for which Vitamin D$_5$ is indicated, for example in a patient experiencing or at risk of such diseases or disorders.

The present disclosure provides for pharmaceutical compositions comprising as an active ingredient, at least one of the compounds of the general Formula I or a pharmaceutically acceptable salt thereof. In some embodiments, the composition can be formulated in a unit dosage form, providing an amount of Vitamin D$_5$ compound ranging from about 0.01 to about 1.0 µg/kg/day and a pharmaceutically acceptable carrier or excipient, to effectively tranquilize the cardiomyocytes present in the overloaded heart. Such tranquilization enables the subject to maintain daily activity without exacerbating the already overworked heart that can lead to progressively worsened cardiac remodeling which includes hypertrophy, loss of myocytes and increased interstitial fibrosis. Methods for tranquilizing the heart are also provided comprising administering a dose of at least one of the Vitamin D$_5$ compounds of the general Formula I or a pharmaceutically acceptable salt thereof in a pharmaceutically acceptable carrier or excipient in a dosage range from 0.01 to about 1.0 µg/kg/day, for example, in a subject experiencing or at risk for developing a cardiac overload disease including any one or more of cardiac hypertrophy, heart failure, decompensated heart failure, cardiomyopathy, myocardial ischemia, coronary artery disease, arrhythmia, hypertension, myocardial infarction and angina.

Vitamin D$_5$ Compounds

Vitamin D$_5$ or 1α-hydroxysitocalciferol or 1-α-hydroxy-2,4-ethyl-9,10-seco-5,7,10(19)-cholestatrien-3 β-ol or 1α-hydroxyvitamin-D$_5$, corresponds in structure to Formula (I) below.

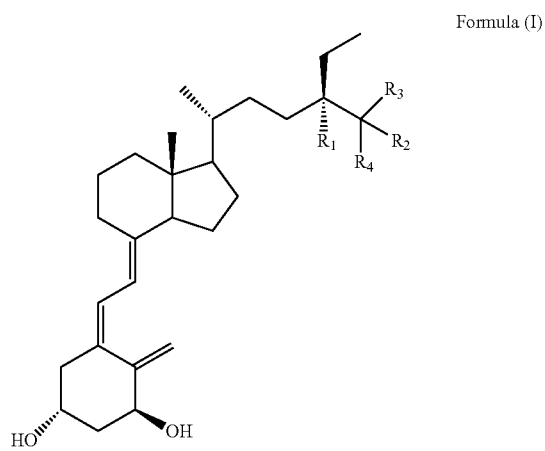

Formula (I)

wherein R$_1$ is hydrogen, R$_2$ is —CH3, R$_3$ is —CH3, and R$_4$ is hydrogen. Methods of making 1α-hydroxysitocalciferol are disclosed in Moriarty, R. M et al., U.S. Pat. No. 6,900,191, which is incorporated herein in its entirety.

In some embodiments, the physiologically active form of Vitamin D$_5$ can be any pharmaceutically acceptable form of Vitamin D$_5$ that is capable of binding to any VDR and exert a biological effect upon that receptor. Preferably, the Vitamin D$_5$ compound exerts an effect upon either of the nuclear and/or membrane VDR in cardiomyocytes. In some embodiments, the biological effect of binding a Vitamin D$_5$ compound to a VDR receptor can include activation of any transcription factor. In some embodiments, the biological effect can be activation of a protein kinase enzyme, for example Protein Kinase C (PKC), Src, or a Ca$^{2+}$ regulatory enzyme such as Sacoplasmic reticulum Ca$^{2+}$-ATPase (SERCA) or phospholamban. Some examples of pharmaceutically active Vitamin D$_5$ compounds include Vitamin D$_5$ analogs described in Moriarty, R. M. et al., U.S. Pat. No. 6,900,191. Generally, an active Vitamin D$_5$ compound can include any Vitamin D$_5$ analog of Formula I, pharmaceutical salts and prodrugs thereof, and any other analogs of Formula I which are hydroxylated in at least one of the C-1, C-22, C-23 C-24 C-25, C-26, C-28 and C-29 position of the molecule.

High doses of Vitamin D$_2$, D$_3$, and D$_4$ can result in hypercalcemia. Non-hypercalcemic Vitamin D compound refers to a Vitamin D compound that has less of a tendency to produce the onset of hypercalcemia than a comparable dosage of calcitriol as assessed by assays well-known to one of skill in the art. Other examples of non-hypercalcemic Vitamin D compounds can be found in U.S. Pat. No. 4,717,721, which is incorporated by reference herein in its entirety.

Pharmaceutical Compositions

The present disclosure provides for pharmaceutical compositions that include at least one Vitamin $D_5$ compound. According to some aspects of the present disclosure, the pharmaceutical compositions contains a Vitamin $D_5$ compound or combinations of Vitamin $D_5$ compounds and is expected to be advantageous for effective rapid modulation of cardiac myocyte contraction, with a prominent decrease in peak shortening. Without wishing to be bound by theory, the pharmaceutical compositions of the present disclosure can produce its pharmacological effects through binding of the Vitamin $D_5$ compound directly to the membrane form of the VDR, which is intimately in association with PKC, in exerting its relaxation effect. In some embodiments, pharmaceutical compositions for the tranquilization of an overloaded heart can include a Vitamin $D_5$ containing compound and one or more pharmaceutically acceptable excipients, carriers, solvents, diluents, excipients, glidants, antioxidants, colorants or fillers which can be used as necessary or desired to form the composition.

In some embodiments, a once daily pharmaceutical composition for the treatment of cardiac overload disease or disorder including left ventricular hypertrophy, heart failure, decompensated heart failure, cardiomyopathy, myocardial ischemia, atherosclerosis, coronary artery disease, hypertension, arrhythmias, angina and chronic renal failure is provided.

Advantageously, the Vitamin $D_5$ compound can be administered to subjects in amounts higher than those indicated for Vitamin $D_3$ due to their non-hypercalcemic effective concentration ranges. Vitamin $D_5$ compounds contemplated herein with or without cardiac relaxants can be safely and effectively administered in dosage amounts ranging from about 0.01 µg/kg to about 5 µg/kg body weight of the subject in a single dose. In some embodiments, the daily dosage range can include from about 0.5 to about 15 µg per day, for example about 0.75, about 1.0, about 2, about 5, about 10, about 12.5 or about 15 µg per day.

In some embodiments, the Vitamin $D_5$ compound can be administered in conjunction with one or more heart relaxants such as a beta blocker, an anti-arrhythmia agent or an anti-hypertension agent. An illustrative example of a beta-adrenergic receptor blocker (beta-blocker) can include one or more of acebutolol, atenolol, betaxolol, bisoprolol, carvedilol esmolol, labetalol, metoprolol, nadolol, penbutolol, pindolol, propranolol, sotalol and timolol. An illustrative example of an anti-arrythmia agent can include adenosine, lidocaine, dofetilde, amiodarone, sotalol, procainimide, verapamil and diltiazem. Illustrative examples of anti-hypertensives can include variously known and prescribed antihypertensive agents including for example $alpha_1$-adrenergic antagonists, beta-adrenergic antagonists, combined alpha/beta-adrenergic antagonists, adrenergic neuron blocking agents, CNS-acting antihypertensives, angiotensin converting enzyme (ACE) inhibitors, angiotensin-II receptor antagonists, calcium channel blockers and diuretic agents. The relative amounts of each cardiac relaxant in the pharmaceutical composition should not exceed the effective amount typically prescribed for patients suffering a cardiac overload disease used on its own. Relative dosages for subjects, particularly human subjects can be readily determined using standard dosing protocols developed for each of the contemplated cardiac relaxants disclosed herein.

In some embodiments, the cardiac relaxant can be administered together with the Vitamin $D_5$ compound or formulated and administered separately. The Vitamin $D_5$ compound can be taken concurrently with the cardiac relaxant, before or after taking the cardiac relaxant. In some embodiments, the cardiac relaxant can be ingested 1 hour, 2 hours, 3 hours or up to 4 hours before or after the administration of the controlled release Vitamin $D_5$ compound to the subject.

In another aspect, the present disclosure provides pharmaceutically effective compositions which comprise a therapeutically-effective amount of a Vitamin $D_5$ compound described above, formulated together with one or more pharmaceutically acceptable excipients and/or carriers (additives) and/or diluents. In some embodiments, the Vitamin $D_5$ compound can be formulated as an immediate release formulation in an oral or injectable dose, with standard pharmaceutically acceptable immediate release excipients. As described in detail below, a controlled release pharmaceutical composition of the present disclosure may be specially formulated for administration in solid or liquid form, including those adapted for the following: oral administration, for example, drenches (aqueous or non-aqueous solutions or suspensions), capsules, tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension of sustained-release formulation; topical application, for example, as a cream, ointment, or a controlled-release patch or spray applied to the skin; sublingually; ocularly; transdermally; or nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable excipient" as used herein means a pharmaceutically-acceptable material, composition, carrier or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each excipient must be "acceptable" in the sense of being compatible with the other components and agents of the formulation and not deleterious to the patient after administration. In some non-limiting examples, pharmaceutically-acceptable excipients can include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; (19) ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants can include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. In some embodiments, a formulation of the present disclosure comprises an excipient selected from the group consisting of cyclodextrins, celluloses, liposomes, micelle forming agents, e.g., bile acids, and polymeric carriers, e.g., polyesters and polyanhydrides. In some embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and mixing with a compound of the present disclosure with liquid carriers, or finely divided solid carriers, or both, and then, if necessary, shaping the product. Formulations of the disclosure suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) each containing a predetermined amount of a Vitamin $D_5$ compound of the present disclosure as an active ingredient. A controlled release Vitamin $D_5$ compound composition of the present disclosure may also be administered as a bolus, electuary or paste.

In solid dosage forms of the disclosure for oral administration (capsules, tablets, pills, dragees, powders, granules, trouches and the like), the Vitamin $D_5$ compound can be mixed with one or more pharmaceutically-acceptable excipients, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as glycerol and paraffin; absorption accelerators, such as quaternary ammonium compounds and surfactants, such as poloxamer and sodium lauryl sulfate; wetting agents, such as, for example, cetyl alcohol, glycerol monostearate, and non-ionic surfactants; lubricants, such as talc, calcium stearate, magnesium stearate, solid polyethylene glycols, sodium lauryl sulfate, zinc stearate, sodium stearate, stearic acid; coloring agents; and controlled release agents such as crospovidone or ethyl cellulose. In the case of capsules, tablets and pills, the pharmaceutical compositions can also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as capsules, pills and granules, may optionally be scored or prepared with coatings and shells, such as enteric coatings and other coatings well known in the pharmaceutical-formulating art. In some embodiments, the present controlled release pharmaceutical compositions can be formulated so as to provide sustained, delayed, pulsed, biphasic or controlled release of a Vitamin $D_5$ compound using, for example, hydroxypropylmethyl cellulose in varying proportions to provide the desired release profile, other polymer matrices, liposomes and/or microspheres. They may be prepared for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient (s) or preferentially, in a certain portion of the gastrointestinal tract, optionally, in a delayed manner. Examples of embedding compositions which can be used include polymeric substances and waxes. The Vitamin $D_5$ compound can also be in micro-encapsulated form, if appropriate, with one or more of the above-described excipients.

The compositions intended for oral use can be prepared according to any method commonly known in the art. The pharmaceutical compositions of the present disclosure can contain one or more agents including non-toxic pharmaceutical excipients which are suitable for the manufacture of tablets. Such excipients can include, for example, an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the one or more Vitamin $D_5$ compounds are mixed with an inert diluent and a controlled and/or immediate release matrix or coating.

Liquid Formulations

Liquid dosage forms for oral administration of the compounds of the disclosure can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Formulation of the present pharmaceutical compositions can also include suspensions. In addition to the active Vitamin $D_5$ the suspension compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of the Vitamin $D_5$ compound(s) of the present disclosure can include powders, sprays, ointments, pastes, creams, lotions, gels, solutions, patches and inhalants. The active Vitamin $D_5$ compound may be mixed under sterile conditions with a pharmaceutically-acceptable carrier, and with any preservatives, buffers, or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a Vitamin $D_5$ compound of the present disclosure to the body. Such dosage forms can be made by dissolving or dispersing the Vitamin $D_5$ compound in the proper medium, for example and organic solvent that is compatible and non toxic. Absorption enhancers can also be used to increase the flux of the compound across the skin. The rate of such flux can be controlled by either providing a rate controlling membrane or dispersing the compound in a polymer matrix or gel.

Pharmaceutical compositions of the present disclosure can be suitable for parenteral administration comprising a Vitamin $D_5$ compound in an inordinate release, or in a controlled release formulation in combination with one or more pharmaceutically-acceptable sterile isotonic aqueous or nonaqueous solutions, dispersions, suspensions emulsions, or sterile powders which may be reconstituted into sterile injectable solutions or dispersions just prior to use. The injectable solutions or dispersions may contain sugars, alcohols, antioxidants, buffers, bacteriostats suspending or thickening agents and other solutes which render the formulation isotonic with the blood of the intended recipient.

One skilled in the art can readily prepare pharmaceutical compositions comprising a Vitamin $D_5$ compound, for example by using the principles set forth in Remington's Pharmaceutical Science, 18th Edition (Alphonso Gennaro, ed.), Mack Publishing Co., Easton, Pa., 1990. In some embodiments, the pharmaceutical compositions of the present disclosure can comprise a Vitamin $D_5$ compound in a immediate or controlled release form.

The preparations of the present disclosure may be given orally, parenterally, topically, or rectally. They are of course given in forms suitable for each administration route. For example, they are administered in tablets or capsule form, by injection, inhalation, eye lotion, ointment, suppository, infusion or inhalation; topical by lotion or ointment. In some embodiments the Vitamin $D_5$ composition can be administered in oral dosages forum. In some embodiments the Vitamin $D_5$ compound is concurrently or at a point either before or after Vitamin $D_5$ administration taken with a cardiac muscle relaxant. In some embodiments, the pharmaceutical composition comprises one or more Vitamin $D_5$ compounds and a cardiac muscle relaxant. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The controlled release formulation of a Vitamin $D_5$ compound may be administered to a subject. The subject may be humans and other mammals, including laboratory animals e.g. rats, mice, rabbits, domesticated animals e.g. dogs, cats, and horses, non-human primates, and monkeys for therapy by any suitable route of administration, including orally, nasally, as by, for example, a spray, rectally, parenterally, intracisternally and topically, as by powders, ointments or drops, including buccally and sublingually. Regardless of the route of administration selected, the Vitamin $D_5$ compounds of the present disclosure, which may be used in a suitable hydrated form, and/or the pharmaceutical compositions of the present disclosure, are formulated into pharmaceutically-acceptable dosage forms by conventional methods known to those of skill in the art.

In general, a suitable daily dose of a compound of the disclosure will be that amount of the compound which is the lowest dose effective to produce a therapeutic effect i.e., a dose which provides binding of a Vitamin $D_5$ compound to a VDR and modulate cardiomyocyte contractility function by enhancing relaxation and decreasing contraction resulting in a reduction in at least one of cardiac index, stroke volume, cardiac mass and E/A ratio. In some embodiments, an effective dose can be a dose of a Vitamin $D_5$ compound wherein the plasma levels of the Vitamin $D_5$ compound in the patient is between about 0.0001 and about 0.01 μg/mL for at least about 12 hours and at least about 24 hours. Such an effective dose will generally depend upon the factors described above. In some embodiments, the Vitamin $D_5$ compound comprising one or more Vitamin $D_5$ analogs which are generally not substantially capable of inducing toxic hypercalcemia (i.e. a plasma calcium concentration of 8.7-10.4 mg/dL or above) as compared to Vitamin $D_2$, $D_3$ and $D_4$ analogs when administered over a period of days, weeks, months or years. Generally, oral, intravenous, and subcutaneous doses of the controlled release Vitamin $D_5$ compound of the present disclosure for a patient, when used for the desired therapeutic effects, will range from about 0.1 μg to about 15 μg per daily dose.

In some embodiments, the once daily controlled release Vitamin $D_5$ compound formulation can be administered with at least one dose of an adjunct cardiac relaxing agent.

Therapeutic Combinations of Vitamin $D_5$ Compounds

In some embodiments, the present compositions and methods can include one or more Vitamin $D_5$ analogs to form a Vitamin $D_5$ compound. In some embodiments, the Vitamin $D_5$ compound is Vitamin $D_5$ analog according to Formula I. In some embodiments, the Vitamin $D_5$ compound can be a mixture of two or more Vitamin $D_5$ analogs described above. In some embodiments, the Vitamin $D_5$ compound can be formulated in an immediate release and/or a controlled release formulation for the tranquilization of an overloaded heart, such as one caused by left ventricular hypertrophy, congestive heart failure, decompensated heart failure, dilated cardiomyopathy, hypertension, angina, myocardial infarction, ischemic heart failure, myocardial ischemia, chronic renal failure and combinations thereof.

Controlled Release Formulations

In some embodiments, the compositions of the present invention comprise one or more controlled release components. In some embodiments, the composition comprises a controlled release composition adapted to release a Vitamin $D_5$ compound according to sustained release profile of dissolution when measured in a U.S.P. type I dissolution apparatus in an acidic pH medium at 100 r.p.m., 372 C. As used herein the term controlled release can include various dosage formulations including sustained release, extended release, prolonged release and delayed release formulations. The controlled release composition can include a controlled release matrix or coating portion comprising a Vitamin $D_5$ compound, a sustained release carrier, and at least one pharmaceutically acceptable excipient. When the composition is initially administered as a single dose, the composition provides a mean plasma concentration of Vitamin $D_5$ compound of at least 0.0001 μg/mL and not more than 0.01 μg/mL within one hour of administration and continues to provide a mean plasma concentration of the Vitamin D compound of not more than 0.01 μg/mL for 12-24 hours. The Vitamin $D_5$ compound can be administered in a dose effective to tranquilize the heart by binding to membrane and/or nucleus VDR and effecting a response on PKC to phosphorylate calcium modulating proteins. In some embodiments, the calcium modulating proteins can be SERCA and phospholamban.

In some embodiments, the controlled release properties exhibit an extended or sustained release pharmacokinetic profile. In some embodiments, the compositions may contain one or more controlled release materials, illustratively selected from two formulation components having different release characteristics. Thus a composition can comprise a first formulation component comprising a Vitamin $D_5$ analog exhibiting a first release profile and a second formulation component comprising the same or different Vitamin $D_5$ analog exhibiting a second release profile. Illustratively, the first release profile can be an immediate release profile and the second release profile can be an extended or sustained release profile. In some embodiments, the first release profile can contain a Vitamin $D_5$ compound in accordance to formula I and the second phase can release a sustained formulation of the same or different Vitamin $D_5$ analog.

In some embodiments, the pharmaceutical compositions of the present disclosure comprising one or more Vitamin $D_5$ compounds can be formulated in one or more distinct release phases, to provide for example a first release profile and a second release profile. In the case of a discrete solid dosage form, the first and second phase formulation components can be more or less intimately co-mixed or blended, or alternatively can form spatially distinct zones of the dosage form.

An illustrative composition has spatially distinct zones comprising a core and a mantle surrounding the core. In such a composition, the mantle can comprise a Vitamin $D_5$ compound exhibiting an immediate release profile containing for example a Vitamin $D_5$ compound and the core can comprise the same or different Vitamin $D_5$ compound for example Vitamin $D_5$ exhibiting an extended and/or delayed release profile.

Another illustrative composition has spatially distinct zones comprising at least two layers. An example of such a composition is a bilayer tablet, wherein one layer comprises a Vitamin $D_5$ compound exhibiting an immediate release profile and the other layer comprises the same or different Vitamin $D_5$ compound exhibiting an extended and/or delayed release profile.

In one embodiment, the composition comprises first and second formulation components as described above, which comprise particles of a first and second kind respectively. For example, the particles of the first kind can exhibit an immediate release profile and the particles of the second kind can exhibit an extended and/or delayed release profile. Illustratively, the particles of the second kind comprise a core comprising the Vitamin $D_5$ compound and an extended and/or delayed release coating comprising the same or different Vitamin $D_5$ compound surrounding the core.

The preparation of controlled release formulations and components are well known within the art. U.S. Pat. Pub. App. Nos. 2005/0175691, 2004/0242640, 2003/0219488 and WO 2005/097191 describe exemplary formulations useful for preparing controlled release formulations of the present invention and are each incorporated by reference herein. In some embodiments, the composition comprises a Vitamin $D_5$ compound, a controlled release component, and at least one pharmaceutically acceptable excipient, wherein the composition upon initial administration of one dose provides a mean plasma concentration of the Vitamin $D_5$ compound of at least 0.0001 μg/mL and not more than 0.01 μg/mL within one hour of administration and continues to provide a mean plasma concentration of the Vitamin $D_5$ compound in the subject that does not exceed 0.01 μg/mL for 12-24 hours. The Vitamin $D_5$ compound is administered in a dose effective to bind to a VDR and modulate cardiomyocyte contractility function by enhancing relaxation and decreasing contraction via activation of the PKC signaling pathway.

In some embodiments, the composition comprises a controlled release composition adapted to release a Vitamin $D_5$ compound according to a biphasic in vitro release profile of dissolution when measured in a U.S.P. type I/II dissolution apparatus in an acidic pH medium at 100 r.p.m., 37° C., where the first phase is an immediate release phase having a maximum duration of 30 minutes and the second phase is a sustained release and wherein 5%-15% of the total amount of the Vitamin $D_5$ compound is released during the initial first phase and the time for release of the remaining 85%-95% of the total amount of the Vitamin $D_5$ compound is between 12 and 24 hours. The Vitamin $D_5$ compound is administered in an effective dose to bind to a VDR and modulate cardiomyocyte contractility function by enhancing relaxation and decreasing contraction via activation of the PKC signaling pathway.

Methods of Tranquilizing an Overloaded Heart Using a Composition Comprising Vitamin $D_5$ Analogs The present disclosure provides a method for preventing, treating and ameliorating cardiac overload diseases having symptoms associated with increased cardiomyocyte contractility and increased force of contraction under cardiac overload conditions. The method generally provides relaxation of the cardiomyocyte and does not improve cardiac function by increasing the force of contraction in the cardiomyocyte.

Clinical Vitamin D3 deficiency and accompanying hypocalcemia are associated with cardiomyopathy. In animal models it has been found that when the animals are normocalcemic, the presence of Vitamin D deficiency results in cardiac hypertrophy and increased cardiac contractility. Weishaar, R., et al. Am. J. Physiol. 253(6 Pt 1): E675-683. The present disclosure provides pharmaceutical compositions useful for tranquilizing the adult cardiomyocyte through intervention at the nuclear and/or membrane VDR with administration of Vitamin $D_5$ compounds, and compositions comprising Vitamin $D_5$ and optionally, a cardiac muscle relaxant acting directly on the cardiomyocyte experiencing cardiac overload or excessive contraction profile.
Determination of a Subject having Cardiac Overload Disease or Risk of Developing Cardiac Overload Disease and End Stage Heart Failure In some embodiments, a subject having a cardiac overload disease can include any subject, preferably mammalian subject, preferably a human subject with a cardiac or cardiovascular disease that imposes a heightened preload or afterload on the subject's heart which can be medically described as pathological. In some embodiments, a subject with a cardiac overload disease can include a subject with left ventricular hypertrophy, heart failure, decompensated heart failure, myocardial ischemia, coronary artery disease, arrythmias, hypertension, atherosclerosis, angina, myocardial infarction and chronic renal failure. A subject who is at risk of developing a cardiac overload disease can also include a subject whose cardiac function may be described as normal, but one in which whose condition if left untreated can develop into one or more of the cardiac overload diseases described above. For example, subjects with hypertension impose a strain on the heart to pump effectively due to the restriction of the subject's blood vessels as a result of the hypertension. That subject is at risk of developing hypertrophy and other cardiac overload diseases if left untreated. In some embodiments, the pharmaceutical compositions of the present disclosure can be administered to a subject having one or more cardiac overload diseases in order to prevent a different cardiac overload disease from occurring. For example, subjects having early stage heart failure (for example Class I or II under the NYHA heart failure rankings) can be treated with the pharmaceutical composition of the present disclosure to prevent the occurrence of end-stage heart failure, (NYHA class IV) or decompensated heart failure.

The field of cardiology has numerous diagnostic and screening tests to diagnose a subject with a cardiac overload disease. Contraction studies of a subject's heart can be performed using any commonly known electrophysiological procedure, including cardiac echocardiogram in combination with ECG/EKG and other electrophysiological techniques. In some embodiments, cardiac hypertrophy can be diagnosed with electrocardiograms using the following indicators: Sokolow+Lyon (*Am Heart J,* 1949; 37:161): S V1+R V5 or V6>35 mm; Cornell criteria (*Circulation,* 1987; 3: 565-72): SV3+R avl>28 mm in men: SV3+R avl>20 mm in women; Framingham criteria (*Circulation,* 1990; 81:815-820): R avl>11 mm, R V4-6>25 mm; S V1-3>25 mm, S V1 or V2+R V5 or V6>35 mm, R I+S III>25 mm; Romhilt+ Estes (*Am Heart J,* 1986:75:752-58) Point score system.

In some embodiments, the degree of cardiac contractility can be determined using non-invasive techniques for example, as described in: Kass, et al., From 'Emax' to Pressure-Volume Relations: A Broader View, Circulation, June, 1988, vol. 77, No. 6. pp. 1203-1212; Kass, et al., "Use of a Conductance (Volume) Catheter and Transient Inferior Vena Cava Occlusion for Rapid Determination of Pressure-Volume Relationships in Man", Catheterization and Cardiovascular Diagnosis, 1988, vol. 15, pp. 192-202; Senzaki, et al., "Single-Beat Estimation of End-Systolic Pressure-Volume Relation in Humans", Circulation, vol. 94, No. 10, Nov. 15, 1996, pp. 2497-2506; Sunagawa, et al., "Estimation of the Hydromotive Source Pressure from Ejecting Beats of the Left Ventricle", IEEE Transactions on Biomedical Engineering, vol. BME-27, No. 6, June 1980, pp. 299-305 and by U.S. Pat. No. 6,090,047.

The terms "treat", "treating" and "treatment" herein will be understood, except where the context demands otherwise, to embrace prophylactic administration to a subject not yet presenting symptoms of a disease or disorder, but at risk of developing the disease or disorder, as well as administration to a subject already having the disease or disorder. Treatment can address an underlying cause of the disease or disorder and/or can be palliative, i.e. act to reduce, alleviate or relieve symptoms that cause distress to the subject.

The subject can be of any animal, particularly mammal, e.g. primate, rodent, domesticated animals, including dogs, cats and horses, but most typically is a human subject.

In some embodiments, the present disclosure provides for a method for tranquilizing the heart of a subject with a cardiac overload disease, the method comprising:

a. providing pharmaceutical composition comprising a Vitamin $D_5$ compound and at least one pharmaceutically acceptable excipient; and b. administering an effective amount of the composition to the subject.

The effective amount of Vitamin $D_5$ tolerated by the patient without adverse side effects, including hypercalcemia and hypercalciuria. Symptoms of hypercalcemia can include fatigue, depression, confusion, anorexia, nausea, vomiting, constipation, pancreatitis or increased urination. Chronic hypercalcemia can result in urinary calculi (renal stones or bladder stones). Abnormal heart rhythms can result, and EKG findings of a short QT interval and a widened T wave suggest hypercalcemia. Severe hypercalcemia can also result in coma and cardiac arrest. These side effects and rebound can be established by a clinician who can relate incidence and severity of side effects and/or rebound effects to plasma Vitamin $D_5$ levels measured by established laboratory techniques in blood samples collected from the subject following Vitamin $D_5$ administration at one or a range of doses, for example intravenously or in a form of an immediate release oral dosage form. Upon establishing a therapeutically effective range tolerated by the subject, a Vitamin $D_5$ composition can be selected having release and/or pharmacokinetic properties consistent with the effective range established.

In some embodiments, the method provides for tranquilizing the subject's heart, specifically, the cardiomyocye experiencing abnormally high peak force by decreasing sarcomere peak shortening. The subject's cardiomyocytes can be tranquilized by administering a pharmaceutical composition containing a Vitamin $D_5$ compound and a pharmaceutically acceptable excipient as provided above. Without wishing to be bound by theory, it is believed that the binding of Vitamin $D_5$ to VDRs located in either the cardiomyocyte membrane and/or the nucleus leads to a normalization or improvement of calcium utilization and thereby producing a direct negative inotropic effect as indicated by a general relaxation of the cardiomyocyte.

The present method steps include administration of a pharmaceutical composition comprising a Vitamin $D_5$ compound in an immediate release or controlled release formulation to a patient experiencing or at risk for developing the cardiac overload disease and/or symptoms associated with the disease, including: heart failure, left ventricular hypertrophy, decompensated heart failure, ischemic cardiomyopathy, dilated cardiomyopathy, myocardial ischemia, atherosclerosis, coronary artery disease, angina pectoris, myocardial infarction, hypertension, cardiac arrythmia and chronic renal failure. In some embodiments, the Vitamin $D_5$ compound can include one or more Vitamin $D_5$ analogs, including Vitamin $D_5$ of Formula I and acceptable salts thereof.

In some embodiments, the present disclosure provides for a method of tranquilizing the heart of a patient with an cardiac overload disease or disorder, the method includes providing a pharmaceutical composition comprising a Vitamin $D_5$ compound and at least one pharmaceutically acceptable excipient; administering an effective dose of the composition to a subject, wherein the pharmacokinetics of the composition exhibits a Vitamin $D_5$ release profile that does not cumulatively induce hypercalcemia in the patient and in which the composition targets the VDR of the overactive cardiomyocyte and provides relaxation to the cardiomyocyte.

In some embodiments, the present disclosure also provides for a method for treating or preventing heart failure in a subject diagnosed as having heart failure or being at risk for heart failure, the method comprising the step of administering to the subject, a pharmaceutical composition comprising a therapeutically effective amount of a Vitamin $D_5$ compound and a pharmaceutically acceptable excipient.

In some embodiments, the present disclosure also provides for a method for reducing at least one of cardiac index, stroke volume and E/A ratio in a subject diagnosed as having either one of cardiac hypertrophy and heart failure or at risk for developing cardiac hypertrophy and heart failure, the method comprising the step of administering to the subject, a pharmaceutical composition comprising a Vitamin $D_5$ compound and a pharmaceutically acceptable excipient. In some embodiments, the pharmaceutical composition can also include a cardiac muscle relaxant as described above.

In some embodiments, a method of tranquilizing the heart of a patient with an overactive myocyte contractile function related disease comprises administering a Vitamin $D_5$ compound in an effective amount. The amount of Vitamin $D_5$ to be administered can vary according to several important variables including: (1) the nature and severity of the cardiac overload disease; (2) the stage in disease progression; (3) the weight and size of the subject; and (4) the likelihood of causing hypercalcemia in the patient using high doses of Vitamin $D_5$. In any event, the dose can be titrated from a low dose to a high dose that provides therapeutic relief to the subject in need thereof by reducing the subject's cardiac force of contraction and increasing the rate of relaxation in the subject's cardiomyocyte. In some embodiments, the pharmaceutical composition can include a unit dose of Vitamin $D_5$ ranging from about 0.01 µg/Kg body weight to about 5.0 µg/Kg body weight of the subject. In some embodiments, the composition exhibits a Vitamin $D_5$ release profile that does not cumulatively induce hypercalcemia in the patient and in which the composition targets the VDR of the overactive myocyte to decrease at least one of cardiac index, heart mass, stroke volume, E/A ratio, and contraction kinetics. In some embodiments, the method also includes increasing or activating PKC activity in the overactive cardiomyocyte above resting levels.

In some embodiments, the cardiac overload disease can be any cardiac disease in which the cardiomyocyte has a decreased rate of relaxation and an increased peak force of contraction that is higher than non-diseased levels. In some embodiments, the diseases related to an overactive contractile function can include: left ventricular hypertrophy, congestive heart failure, decompensated heart failure, dilated cardiomyopathy, angina, myocardial infarction, myocardial ischemia, coronary artery disease, hypertension, chronic renal failure and the like. The administration of a pharmaceutical composition of the present disclosure comprising one or more Vitamin $D_5$ analogs and a pharmaceutically acceptable excipient, operates in some embodiments, to tranquilize the cardiomyocyte by restoring proper $Ca^{2+}$ ion transport in the cell and induces specific changes in sarcomere shortening and relaxation. In particular, administration of an effective amount of a Vitamin $D_5$ compound accelerates the relaxation rate and decreases peak shortening of the myocyte sarcomeres via PKC phosphorylation of target proteins, for example, phospholamban and troponin C I, in a fashion that is unrelated to endothelin activation of PKC.

As used herein, the methods of the present disclosure affords preventative and therapeutic benefit to subjects having a cardiac overload disease. In some embodiments, a subject in early stages of heart failure, can be treated with an effective dose of a pharmaceutical composition of the present disclosure to prevent the patient from progressing to a more advanced stage of heart failure in accordance with the New York Health Association Standards of Heart Failure. Alternatively, the hypertensive patient without clinical signs of heart failure can in addition to commencing a Vitamin $D_5$ regimen, also treat the underlying factors that are causing the cardiomyocytes to become overactive, for example, by co-administering a cardiac relaxant such as a beta-adrenergic receptor blocker, and/or other negative inotropic agents in combination with a Vitamin $D_5$ composition.

Dosages

Vitamin D toxicity (hypervitaminosis D) induces abnormally high serum calcium levels, i.e. plasma calcium at 8.7-10.6 mg/dL (hypercalcemia), which could result in bone loss, kidney stones, and calcification of organs like the heart and kidneys if untreated over a long period of time. Since the consequences of hypercalcemia are severe, the Food and Nutrition Board established a very conservative upper limit of 2,000 IU/day for children and adults. Research published since 1997 suggests that the upper limit for adults is likely overly conservative and that vitamin D toxicity is very unlikely in healthy people at intake levels lower than 10,000 IU/day. (Linus Pauling Institute, Micronutrient Research for Optimum Health, Oregon State University)

As used herein, the methods of the present disclosure affords preventative and therapeutic benefit to subjects having a cardiac overload disease. In some embodiments, a subject in early stages of heart failure, can be treated with an effective dose of a pharmaceutical composition of the present disclosure to prevent the patient from progressing to a more advanced stage of heart failure in accordance with the New York Health Association Standards of Heart Failure. In some embodiments, a patient tested as having a diagnosis of cardiac overload as manifested by overactive cardiomyocyte contractile function, such as a hypertensive patient with no clinical indications of heart failure, can prevent the occurrence of heart failure by commencing a therapy using a relatively low dose, i.e., a pharmaceutical composition containing an effective amount of Vitamin $D_5$ analog in an amount less than 15 µg of Vitamin $D_5$ per day, less than 10 µg of Vitamin $D_5$ per day, less than 1.0 µg of Vitamin $D_5$ per day and less than 0.5 µg of Vitamin $D_5$ per day in a pharmaceutical composition comprising a pharmaceutical excipient and proceed stepwise to a higher dose if needed. If desired, the daily dose of Vitamin $D_5$ can be administered in a plurality of dosage forms, but most conveniently, a single dosage form contains the full daily dose.

Alternatively, the subject without clinical signs of a cardiac overload disease, for example, heart failure, can in addition to commencing a Vitamin $D_5$ regimen, also be treated by ameliorating or treating the underlying factors that are causing the cardiomyocytes to become overactive, for example, by co-administering a cardiac relaxant such as a $beta_1$-blocker, and/or other negative inotropic agents in combination with a Vitamin $D_5$ composition.

An exemplary dosing regimen can include up to 1.0 µg/Kg body weight Vitamin $D_5$ compound delivered orally, intramuscularly, intraperioneally, intravenously, intraclermally, or in any other medically relevant method daily for 9-15 weeks or equivalents thereof, would provide the equivalent of about 0.5 to about 100 micrograms of a Vitamin $D_5$ compound per day or at least about 1 microgram of a Vitamin $D_5$ compound by enteral or parenteral administration three times weekly or its equivalence. For 1α-hydroxysitocalciferol, a suitable dosing regimen would provide the equivalent of about 0.1 to about 15 micrograms 1α-hydroxysitocalciferol daily or at least about 1 microgram 1α-hydroxysitocalciferol administered three times weekly as a bolus. Suitable dosing regimens for other Vitamin $D_5$ analogs, 1α25, 1α26, 1α28, 1α29 dihydroxy sitocalciferol or the 22,23 dihdro analogs thereof, can be determined straightforwardly by those skilled in the art based on the therapeutic efficacy of the Vitamin $D_5$ compound to be administered.

The dosing regimen can include a single dose for example for acute therapy, or once daily dosing for several days, usually at least 7 days. A dose or doses used to provide pharmacokinetic data in test subjects should be similar to the dose desired to be administered to the subject with the disease or disorder. By "similar" in the present context is meant equal, or sufficiently close that, by reasonable interpolation or extrapolation from the data, pharmacokinetic properties for the desired dose can be reasonably estimated by those skilled in the art.

In some embodiments, the pharmaceutical composition used according to the present disclosure provides a Vitamin $D_5$ compound formulated in an immediate release or a controlled release pharmaceutical composition comprising at least one Vitamin D5 compound, wherein the at least one Vitamin $D_5$ compound when administered orally to a plurality of test subjects once daily in an amount delivering a Vitamin $D_5$ dose of about 0.1 to about 15 micrograms/day, exhibits Vitamin $D_5$ release properties providing a 24-hour profile of plasma Vitamin $D_5$ concentration averaged over the test subjects, that does not substantially or protractedly fall below about 0.0001 µg/mL and does not substantially or protractedly exceed 0.01 µg/mL. In some embodiments, the plasma Vitamin $D_5$ concentration neither substantially nor protractedly falls bellow about 0.0005 µg/mL, about 0.001 µg/mL, about 0.005 µg/mL or about 0.0075 µg/mL. In some embodiments, the plasma Vitamin $D_5$ concentration neither substantially nor protractedly exceeds about 0.005 µg/mL, about 0.001 µg/mL or about 0.0005 µg/mL. With respect to the terms "substantially" or "protractedly" in the present context, the following situations are illustrative. A concentration that is within about 20%, for example within about 10%, below a stated minimum or above a stated maximum is considered not to "substantially" fall below or exceed the stated minimum or maximum respectively. A concentration that temporarily falls below a stated minimum or exceeds a stated maximum for a period of less than 2 hours, for example less than about one hour, is considered not to "protractedly" fall below or exceed the stated minimum or maximum respectively.

An effective dose or amount of the Vitamin $D_5$ compound can also be one in which the Vitamin $D_5$ compound is able to bind to the subject's cardiomyocyte VDR and modulate cardiomyocyte contractility function by enhancing relaxation and decreasing contraction via activation of the PKC signaling pathway. In some embodiments, the method further includes administering a Vitamin $D_5$ compound comprising one or more Vitamin $D_5$ analogs and a pharmaceutically acceptable excipient or carrier.

Further enabling disclosure of how to make and use the pharmaceutical compositions and methods for preventing and treating a cardiac overload disease or disorder in vivo as described above are provided in the following non-limiting examples.

Example 1

PKC Activation Above Resting Levels

Vitamin $D_5$ induces accelerated relaxation in adult cardiomyocyte contractile function via PKC activation. The accelerated relaxation of cardiomyocyte contractility can also be found to occur with sarcomere shortening in an acute response that is not correlated with nuclear VDR activation. In addition to continued acceleration of relengthening in cardiomyocytes, upon administration of Vitamin $D_5$ the PKC targets phospholamban and cardiac troponin I (cTnI) are specifically phosphorylated by PKC within approximately 60 minutes. Without being bound to theory, it is believed that phosphorylation of phospholamban can increase $Ca^{2+}$ sequestration into the sarcoplasmic reticulum while cardiac troponin C I phosphorylation decreases myofilament $Ca^{2+}$ sensitivity, two particularly significant events in increasing the relaxation of contractile function in the adult cardiomyocyte.

The pharmaceutical compositions and methods described herein illustrate a mechanism to accelerate relaxation of cardiomyocyte contractile function via direct and rapid cellular action upon administration of 1α25-dihydroxyvitamin $D_5$. These acute effects can be blocked by PKC inhibitors, illustratively bis-I. The phosphorylation of these key cardiac markers phospholamban and troponin C I develop within the same time period as the initial rapid decrease in peak shortening, and acceleration of contraction and relaxation rates.

Example 2

VDR Knockout Mouse

Several laboratories have characterized the effects that modification of the Vitamin D endocrine system has on cardiac muscle structure and function. It has been shown that Vitamin $D_3$ deficiency alters rat myocardial morphology, ECM and function. The inventor of the present disclosure has shown that large and statistically significant increases in ventricular pressure development (+dP/dt) are observed in perfused hearts from young (9 weeks old) Vitamin $D_3$-deficient rats compared to hearts from Vitamin $D_3$-sufficient rats. A mechanism by which myocardial contractility can be increased is by raising intracellular calcium concentrations. It has been shown that 9-week-old vitamin $D_3$-deficient rats had an increase of L-type calcium channels and post rest contraction response, a measure of sarcoplasmic reticulum calcium uptake. Heart failure (HF) affects nearly 5 million people in the United States alone and at present no single unifying hypothesis can account for the etiology of this disease. However, it is known that neuroendocrine factors and cytokines are associated with HF and that left ventricular remodeling is an important determinant in the progression to heart failure. Reduced levels of the most active Vitamin D metabolite, 1,25-dihydroxyvitamin $D_3$ are associated with an increased risk of heart failure and reports also indicate ventricular function is compromised and a dilated cardiomyopathy develops in pediatric patients with rickets caused by a Vitamin D deficiency. Thus, the study of the cardiovascular effects of VDR ablation in mice is important and relevant to human disease.

Mouse Breeding, Housing and Feeding

Wild-type [WT] VDR (+/+), heterozygous (+/−) and VDRKO (−/−) mice were produced from VDR(+/−) originally the generous gift of Dr. Marie Demay, Mass. General Hospitals. All mice, breeders and offspring were housed in an animal facility with a 12:12-h light-dark cycle and fed a rodent chow containing 2% Ca, 1.25% phosphorus and 20% lactose. Age-matched WT(+/+), heterozygous (+/−) and VDRKO(−/−) mice were genotyped and used in these experiments.

Measurement of Myocardial Heart Weight/Body Weight Ratio

Mice were weighed and then killed via cervical dislocation. The chest cavity was rapidly opened, and the heart removed and rinsed in two washes of ice-cold saline. Major blood vessels and connective tissue was removed, the heart blotted dry, weighed, and the heart weight/body weight ratio calculated. Other organ weights were determined and weight to total body weight ratios calculated as shown in FIG. 1 and FIG. 2. It can be seen that upon removal of the VDR, the mice develop statistically significantly bigger heart weight/body ratios as compared to wild type. No other organ is as statistically affected as that of the heart.

Measurement of Serum Calcium, Phosphate and Magnesium

Blood calcium (Arsenazo III), ionized calcium (NOVA ISE), phosphate (Phosphomolybdate), and magnesium (Formazan Dye) were measured by the Special Chemistry Clinical Laboratories, University of Michigan Hospital. As shown in FIG. 3, no statistically significant difference was observed between the knockout and wild type animals.

Measurement of Ang II, Aldosterone and Renin Activity

Blood angiotensin II and aldosterone levels were measured by radioimmunoassay from commercially available kits. Plasma renin activity was measured assessing enzyme activity.

Non-Invasive Recording Electrocardiograms in Conscious Mice

The System used was the AnonyMOUSE ECG Screening System (Mouse Specifics, Boston, Mass.). The mice were placed on the instrument's platform and acclimate for 10 min prior to ECG recordings. Data were analyzed by propriatal software and all mice ECG intervals analyzed by Student's two-tail t-test.

Non-Invasive Blood Pressure Measurement by External Tail Pulse Detection

To obtain an accurate blood pressure reading, mice remained still and unperturbed throughout the measurement period. Mice were conditioned to the restraint and the warming chamber for 10-20 min/day for at least 3 days before measurements. After this 3-day training period, mice typically remained relatively still and unperturbed when placed in the restrainer on the day of testing. The chamber (model 306 warming chamber, IITC Life Science; Woodland Hills, Calif.) was kept at 31-33° C., and a darkened nose cone helped calm and secure the mouse in the restraint (model 84 mouse restrainers, IITC Life Science). An integrated sensor-cuff occluder (model B60-1/4, IITC Life Science) operated to stop tail pulsation on inflation and to detect the return of tail pulsations (RTP) passing through the occluder cuff on each deflation cycle. The RTP-computerized blood pressure monitor (model 6M 229 6 channel mouse system, IITC Life Science) was set for desired sensitivity, number of cycles, the maximum tail-cuff inflation pressure, the rate of deflation, and the interval between cycles. The maximum pressure of inflation was set 20-40 mmHg above anticipated systolic pressure. The instrument was set for a maximum inflation pressure of 200 mmHg for mice that were expected to have pressures in the normal range and was increased to 250 or 300 mmHg for markedly hypertensive mice. After 5-10 min of stabilization in the chamber, a typical run involved 10 repetitions of the automated inflation-deflation cycle. Statistical significance was determined by the two-tail Student t-test.

Results

FIG. 1 shows the heart weight body weight ratio of VDR wild type (+/+), knockout (−/−) and heterozygous (+/−) mice. There was a significant 41% [P<0.005] increased HW/BW ratio for the VDRKO hearts relative to the VDRWT mice hearts. Heterozygous (+/−) mice had an increased 14% [P<0.05] HW/BW ratio relative to WT. FIG. 2 is data obtained from the analysis of liver, kidney, brain and tibia for organ weight/body weight ratios for the KO(−/−), WT(+/+) and HET(+/−) mice. The data show that for liver, kidney and tibia VDRWT, VDRKO or heterozygous genotypes, no significant changes in organ weight/body weight ratios were observed. We have not investigated the significance of this observation. The data reveal specificity of organ hypertrophy. FIG. 3 shows blood total calcium levels, phosphate levels and magnesium levels in the VDRKO, VDRWT and heterozygous mice. No significant changes were observed.

With reference to FIG. 4, the graph shows systolic and mean arterial blood pressure at 3, 6 and 9 months for the VDRKO and VDRWT mice. At 3 and 6 months no significant changes were observed for VDRKO versus VDRWT in systolic or mean arterial pressure. However at 9 months systolic blood pressure was significantly lower in the VDRKO than the VDRWT mice [P<0.05]. FIG. 5 shows the angiotensin II and aldosterone levels in the blood from the VDRKO, VDRWT, and heterozygous mice. No significant changes in angiotensin II or aldosterone level were observed. FIG. 6 shows the plasma renin activity of 3 pooled [2-4 mice per pool] mice plasma samples of VDRKO and 3 pooled plasma samples from VDRWT mice. An increased level of renin activity was observed in the VDRKO mice but this 50% increase was not significantly different. Significance was assessed for n=3 assays for VDRKO and VDRWT. ECG analysis in the intact KO, HETERO or WT mice was performed. ECG analysis showed no significant differences in the intact KO, HETERO or WT mice at 3, 6 and 9 months. The absence of QRS elongation in the VDRKO mice supports the measured normal serum calcium levels.

Results from the experiments on knock-out VDR mice show the effects of ablation of the Vitamin D receptor and signaling on adult mouse heart structure. The data shows that profound cardiac hypertrophy is apparent at 12 months of age for the VDRKO mouse. Relative to our previous studies with vitamin D deficient rats the increase in heart weight to body weight was much greater in the VDRKO mouse (41%) relative to the level of hypertrophy in 9- or 18-month-old Vitamin D deficient rat (18%). This increase in hypertrophy (>2-fold) as a result of VDR ablation could be a result of incomplete depletion of Vitamin D in the rats on vitamin D deficient diets in our previous studies or the age of the animals.

Recent reports have suggested that the observed cardiac hypertrophy seen in VDRKO mice is a consequence of activation of both the systemic and cardiac RAAS, and support the notion that 1,25-dihydroxyvitamin $D_3$ regulates cardiac function, at least in part, through the RAS. Our data do not directly contradict this possibility but do show that in the absence of significant increases in renin, angiotensin II, aldosterone, or blood pressure, cardiac hypertrophy as a result of VDR knockout occurs and is significantly greater (41% versus 20%) at 12 months than reported at 3 months. This prior study used VDRKO mice transferred to the high calcium and lactose diet for a period of 5 weeks. In the present study, mice were bred from mothers on the high calcium diet and maintained on it for the entire 12 months of the study. This is the most apparent difference in the two studies. Interestingly, it is recognized that high calcium diets decrease plasma renin activity, reduce angiotensin II receptors and increase sodium excretion. Recently, high calcium diets were shown to down regulate kidney angiotensin converting enzyme (ACE) and thus decrease blood pressure. Thus, our observation of a trend toward increased renin level but normal blood pressure, angiotensin II and aldosterone levels could be a result of the length of time (12 months) high calcium diets were fed to mice in our study and the concomitant decreased expression of ACE.

Example 3

Induction of VDR and Atrial Natriuretic Peptide (ANP) in HL-1 Cardiomyocytes After Exposure With Vitamin $D_3$ and Vitamin $D_5$ Induction of VDR and repression of ANP by calcitriol (1,25-$(OH)_2$vitamin-D3) and 1 alpha analogs (1α-Hydroxyitamin-D3 and 1α-hydroxysitocalciferol) is shown in the Western blot of FIG. 7. HL-1 cardiomyocyte cells were grown until confluent then split, and an equal amount ($8 \times 10^6$ cells) of cells were plated for 24 hours and then treated for 48 hours either with vehicle (control) or with the indicated amount of Vitamin D compound. Cells were then harvested and subjected to Western analysis. Actin shows the equal relative amount of protein run per lane. The data demonstrate considerable induction of VDR by all three analogs and remarkable repression of ANP expression by 1α-hydroxysitocalciferol.

Example 4

Measurement of Heart Tranquilization In-Vivo in Heart Failure Rats Administered with Vitamin D Analogs The effects of Vitamin D compounds including Vitamin $D_5$ and $D_3$ on the contraction of cardiomyocytes in vivo can be studied using normal and heart failure prone rats. To test the effect of Vitamin D compounds on heart failure rats, the present inventors selected the strain of rats called Spontaneously Hypertensive Heart Failure (SHHF) rats obtained from Charles River Laboratories, Wilmington Mass., USA. The SHHF rat was developed by backcrossing the SHROB rat to the SHR/N rat. They are characterized as naturally developing congestive heart failure, hypertension, nephropathy, obesity, insulin resistance, hyperinsulinemia and Type 2 diabetes spontaneously. The SHHF rat exhibits the following traits: hypertension (100 percent), obesity (25 percent), and CHF (100 percent in recent sibships). Obesity is expressed as an autosomal recessive (cp/cp) trait, and hypertension is multifactorial (Yen at al., 1974). The CHF trait has been maintained through at least 15 generations. The mode of inheritance of the CHF is probably multifactorial, much like hypertension. These rats develop many of the clinical signs of CHF: generalized and subcutaneous edema, hydrothorax, ascites, dyspnea, cyanosis, enlarged hearts, left atrial thrombosis, and hyperemia of the lungs, liver, and kidneys. These rats are hypertensive, but blood pressure falls to normal levels with the onset of severe CHF. Other cardiac dynamics of the SHHF rat include an area fraction of fibrous tissue, consisting of replacement and interstitial fibrosis, is typically increased in all three ventricular walls in CHF rats and tended to be most pronounced in the inner one-third of the LVFW. These morphologic changes probably reflect early compensatory LV hypertrophy at 6-10 months of age. This is followed by LV failure with elevated right heart pressures and RVFW hypertrophy, finally leading to biventricular CHF. This progression is similar to that of hypertensive heart disease in humans. Other similarities between the SHHF model and human hypertensive-diabetic cardiomyopathy (Factor et al., 1980) and another rat model of hypertension and diabetes (Factor et al., 1983) include increased heart weight and prominent interstitial fibrosis. Pathologic alterations in SHHF Rat hearts corresponding to human dilated cardiomyopathy include four-chamber dilation, intracardiac thrombi, myocyte hypertrophy, and interstitial fibrosis (Unveferth et al., 1986).

The SHHF rat has served as a valuable in-vivo model for studying the effects of various human heart failure medicines and are directly correlated to human heart failure pathology. (See: Willett, R. N., et al. (1999) "In Vitro and In Vivo Characterization of Intrinsic Sympathomimetic Activity in Normal and Heart Failure Rats" *J. Pharmacol. and Exp. Therapeutics* 289(1): 48-53. See also, Heyen, J. R. R. et al., (2002), "Structural, functional, and molecular characterization of the SHHF model of heart failure" *Am. J. Physiol. Heart Cir. Physiol.* 283: H1775-H1784.) These references are hereby incorporated herein in their entireties.

Five treatment groups were established using SHHF rats. In each cohort (5-6 rats), the diets were substantially identical, rats were each fed a high salt diet (8% NaCl) (Harlan Teklad diet TD92012, Madison Wis. USA) and were accommodated equally. All treatment groups received a single once daily administration subcutaneously (SQ) of a Vitamin D compound at varying concentrations five times per week. The Vitamin D compound was dissolved in 1,2 propandiol containing 0.7% ethanol. Control SHHF rats were dosed with vehicle control alone. The animals were dosed for a period of 13 weeks before they were examined by echocardiography explained in more detail below. The first group comprised a control group in which they received a vehicle alone treatment lacking any Vitamin D. The second group consisted of SHHF rats injected with 18 ng 1,25 dihydroxy Vitamin $D_3$ per dose, one dose per day treated animals. The third group consisted of SHHF rats injected with 33 ng of 1α-hydroxysitocalciferol per dose, one dose per day treated animals. The fourth group consisted of SHHF rats injected with 100 ng of 1α-hydroxysitocalciferol per dose, one dose per day treated animals. The fifth group consisted of SHHF rats injected with 300 ng of 1α-hydroxysitocalciferol per dose, one dose per day treated animals.

Measurement of Heart Rate, Blood Pressure and Body Weight

Blood pressure measurement by tail-cuff artery occlusion. After the drug (e.g. 1α-hydroxysitocalciferol treatment, the systolic and diastolic blood pressures were measured by the tail cuff method (Visitech Systems, Apex, N.C., USA). The rats that were habituated to the procedure were laid on the warming chamber and their blood pressure was recorded from the tail. Similarly, at the end of the Vitamin D treatment period, the rats were also weighed and their resting heart rates were recorded. As shown in FIG. 8, there was an increase in heart rate of the 300 ng/day Vitamin $D_5$ treated rats over the control. Similarly, the Vitamin D3 treated rats were also found to have higher heart rates albeit not statistically significant over the control SHHF rats or the Wistar rats.

Elevated blood pressure is considered to be a predictor of developing several cardiac overload diseases, including congestive heart failure, left ventricular hypertrophy, myocardial ischemic disease, coronary artery disease including arteriosclerosis or atherosclerosis, renal failure and aneurisms. The results in FIG. 9 illustrate that the tranquilization of the heart is most likely independent of blood pressure reduction as found to occur with the use of ACE-inhibitors and Angiotensin (II) receptor blockers.

As shown in FIG. 10, the total body weight for most of the treatments and controls were similar with the exception of the 100 ng/day Vitamin $D_5$ treated rats.

Cardiac Hemodynamic Parameters Measured with Echocardiography

After 13 weeks of treatment with the Vitamin D compounds or vehicle control alone, the SHHF rat's cardiac hemodynamic condition was measured, recorded and analyzed for the presence or absence of cardiac tranquilization and reversal of heart failure symptoms.

Non-invasive recording electrocardiograms and echocardiography in conscious rats: Two-dimensional and M-mode echocardiographic images will be recorded using a GE S10 MHz phased-array transducer, connected to a General Electric, Vivid 7 Ultrasound System. The System used for ECG was the AnonyMOUSE ECG Screening System (Mouse Specifics, Boston, Mass. USA). The rats are placed on the instrument's platform and acclimated for 10 min prior to ECG recordings. Animals are anesthetized using an isoflurane anesthetic machine, first by introducing 4% isoflurane and 1 liter of oxygen to an induction chamber. When rats are in lateral recumbency and the breathing is slowed, they are moved to the table where they are placed on a warming pad to maintain body temperature. Their nose is placed in a cone which supplies 1-2% isoflurane and 1 liter of oxygen to maintain a surgical plane of anesthesia. The hair is removed from the upper abdominal and thoracic area with depilatory cream. ECG is monitored via non-invasive resting ECG electrodes (trimmed to fit) placed on the paw pads. The echocardiogram takes approximately 10 minutes.

Transthoracic echocardiography is performed in the supine or left lateral position. Data are analyzed by proprietal software and all rats ECG intervals analyzed by Student's two-tail t-test. The following M mode echocardiographic measurements will be made: Duration of A wave; Peak A wave at septal annulus; Body weight; Cardiac index; Deceleration time of mitral inflow E wave; E wave-to-A wave ratio; Ratio of peak E waves mitral/septal annulus; Ejection fraction; Fractional shortening; Peak E wave at septal annulus; Ratio of E/A at septal annulus; Heart rate; Isovolumic relaxation time; Intraventricular septum in diastole; Intraventricular septum in systole; Left ventricular mass; Left ventricular mass-to-body weight ratio; LV dimension in diastole; LV dimension in systole; Left ventricular ejection time; Peak velocity of A wave at the mitral valve; Peak velocity of E wave at the mitral valve; Change in IVS thickness; Change in posterior wall thickness; Peak A wave velocity in the pulmonary vein; Ratio of pulmonary vein/ mitral valve A wave durations; Peak of A wave in the posterior wall; Peak of E wave in the posterior wall; Posterior wall thickness in diastole; E/A wave ratio in the posterior wall; Posterior wall thickness in systole; ECG R-R interval; Relative wall thickness; Stroke volume; Duration of the pulmonary venous A wave; Velocity of circumferential shortening; LV diastolic volume; LV systolic volume. Doppler measurement of rates of valve contracture, blood flow and muscle contractile parameters were obtained.

Stroke Volume

As shown in FIG. 11, the control SHHF heart failure rats treated with vehicle control has a basal stroke volume of approximately 420 microliters ($\mu L$) of blood per heart beat. Increasing the stroke volume in a subject with cardiac overload disease is a predictable result of poor cardiac performance. As the heart fails to adequately deal with the cardiac demands of the body, a Frank-Starling mechanism takes place in which an increased preload helps to sustain cardiac performance. Hypertrophy of the myocardium, caused by the terminally differentiated heart muscle fibers increasing in size in an attempt to improve contractility and increase the stroke volume is required to meet demand. This may contribute to the increased stiffness and decreased ability of the cardiomyocytes to relax during diastole. However, the heart failure heart develops maladaptive mechanisms in response to increased cardiac stroke volume resulting in increased myocardial oxygen demand, myocardial ischemia, impaired contractility and arrythmogenesis.

The overloaded heart can benefit from a tranquilization effect that promotes improved heart muscle contractility by improving myocardial relaxation (lusitropy) while reducing the overall stroke volume. The reduction in stroke volume is believed to be an indicator that the overloaded heart can pump less volume and yet accommodate perfusion demands. As the overloaded heart improves in its response to increased wall stress, the net effects of these maladaptive mechanisms on cardiac hypertrophy and myocardial remodeling is diminished. Similarly, by responding to increased cardiac demands with a relaxation of the heart, the present treatment with Vitamin $D_5$ may avert the pathological effects of neurohormonal derangements, most notably, activation of the rennin-angiotensin-aldosterone system (RAAS) that act to maintain arterial pressures and perfusion of vital organs. One of the deleterious effects of the neurohormonal compensatory effects is to increase cyclic adenosine monophosphate (cAMP) which causes an increase in calcium entry into the myocytes which augments myocyte contractility but impairs myocyte relaxation.

FIG. 11 shows that in SHHF rats untreated with Vitamin $D_5$, the stroke volume is statistically significant in comparison to all doses of Vitamin $D_5$. Most pronounced, is the effect of reducing the stroke volume in these hypertensive and heart failure rats when the rats are administered with 300 ng per day of Vitamin $D_5$.

Cardiac Index

Similarly, cardiac index is a measure of cardiac blood output per unit time, per unit surface area. Typically, a normal cardiac index in a subject with no disease ranges from 2.5-4.2 $L/min/m^2$. In a heart failure patient, the aim is to bring their cardiac index to at least 2.5 $L/min/m^2$. Increasing the cardiac index with positive inotropic agents (agents that increase the force of the heart's contraction) however, has severe problems relating to increasing the myocardial oxygen demand. Moreover, increasing the myocardial work stress leads to increased risk of arrythmias. FIG. 12 shows that treatment with Vitamin $D_5$ at 300 ng/day produced a significant reduction in cardiac index in comparison to control SHHF rats and Vitamin D$_3$ treated rats while maintaining similar heart rates to the other tested groups. As shown in FIG. 12, the hypertensive and heart failure rats treated with Vitamin D$_5$ showed a dramatic tranquilization effect on the heart as shown by a statistically significant reduction in cardiac index in the absence of decreased heart rate.

E/A Ratio

The elevated E/A ratio of the transmitral flow, the short deceleration time, the reduced S/D ratios of the pulmonary venous flow, the lower S pulmonary venous velocity and the pseudo-normal and restrictive diastolic patterns serve to characterize functional heart failure classes III and IV of the New York Hear Association. The clinical and functional class improvement in congestive heart failure patients is often accompanied by a reduction in the E/A transmitral flow ratio and by an augmentation of the deceleration time (See Shen W F, Tribouilloy C, Rey J L, et al. Prognostic significance of Doppler-derived left ventricular diastolic filling variables in dilated cardiomyopathy. *Am Heart J* 1992; 124: 1524-33).

Diastole starts with isovolemic relaxation, which is an energy-dependent process, followed by rapid ventricular filling, and finally atrial contraction. Factors affecting either phase may contribute to diastolic dysfunction (DD). Impairment of diastolic filling as a result of DD leads to elevated pulmonary pressures and ultimately pulmonary congestion or edema, which gives rise to the clinical symptoms and signs of diastolic heart failure. DD may develop from factors either intrinsic or extrinsic to the left ventricle. Intrinsic factors causing DD occur primarily as one of 2 mechanisms: (1) impaired relaxation; (2) increased stiffness. Extrinsic factors, such as pericardial restriction, may also cause DD.

Ventricular diastolic relaxation, an energy-dependent process, may be impaired by decreased energy availability or by changes in calcium homeostasis. ATP is required for actin-myosin crossbridge dissociation and the reuptake of calcium into the sarcoplasmic reticulum. Conditions associated with decreased ATP availability, such as ischemia, increased diastolic calcium concentration, or a delay in the decline of diastolic calcium concentration, may impair relaxation. Removal of calcium from the cytosol may be delayed by decreased activity of sarcoplasmic reticulum calcium ATPase (SERCA) or an increased level of activity of phospholamban (a SERCA inhibitory protein). Decreased SERCA and increased phospholamban may occur with ventricular hypertrophy secondary to hypertension or aortic sclerosis.

Measurement of diastolic function is complex and dependent on loading conditions of the heart. Multiple parameters may be measured. Two such parameters are transmitral velocity and deceleration time. Blood flow across the mitral valve occurs in 2 phases: an early transmitral flow (E wave) and a late flow with atrial contraction (A wave). The relative contribution of each is expressed as a ratio (E/A). An E/A ratio less than 0.75 or greater than 1.5 indicates DD.

The results of the present study in FIG. 13 indicates that administration of Vitamin D$_5$ at least 100 ng/day provides a significant reduction of the E/A transmitral flow ratio to a ratio that is indicative as normal (i.e. between 0.75 and 1.5). With the 300 ng/day treatment of Vitamin D$_5$, the E/A ratio observed in the SHHF rats returned to a normal level of about 0.99 within the 13 week treatment regimen. In contrast, the control untreated SHHF rats and the Vitamin D$_3$ (18 ng/day) and the Vitamin D$_5$ (lower dose of 33 ng/day) treated animals had an E/A ratio of 1.6 or higher. The diagnostic significance of a high E/A ration as a predictor for morbidity and increased risk of mortality due to heart failure is well documented. ("In a population-based sample of middle-aged and elderly adults, mitral E/A>1.5 at baseline Doppler echocardiography is associated with 2-fold increased all-cause and 3-fold increased cardiac mortality rate independent of covariates; . . . " pg. 1932 in Bella, J. N. et al., Mitral Ratio of Peak Early to Late Diastollic Filling Velocity as a Predictor of Mortality in Middle-Aged and Elderly Adults: The Strong Heart Study" Circ.: Published Online Apr. 1, 2002 (http://circ.ahajournals.org/cgi/content/full/105/16/1928). It appears that Vitamin D$_5$ at the higher doses of 100 and 300 ng/day reversed clinical in vivo symptoms of heart failure in the SHHF rat, possibly extending the hypothesis of preventing end-stage decompensated heart failure in subjects with early or moderate heart failure or other cardiac overload diseases such as cardiac hypertrophy, ischemic heart disease, cardiomyopathy, hypertension, myocardial infarction and coronary artery disease.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for treating a subject diagnosed with cardiac hypertrophy, increased cardiac interstitial fibrosis, or hypertension, said method comprising the step of administering to the subject, a pharmaceutical composition comprising a therapeutically effective amount of 1α-hydroxysitocalciferol and a pharmaceutically acceptable excipient, wherein the 1α-hydroxysitocalciferol has the structure

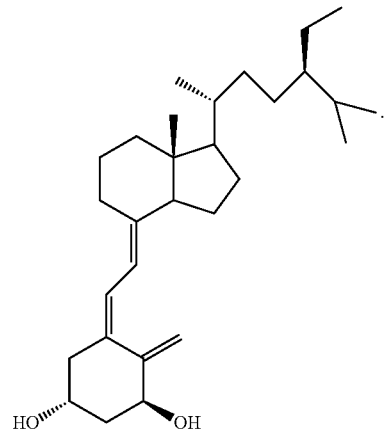 [SMILES: C=C1/C(=C\C=C2/CCC[C@@]3(C)C2CCC3[C@H](C)CC[C@@H](CC)C(C)C)C[C@@H](O)C[C@@H]1O]

2. The method according to claim 1 wherein the 1α-hydroxysitocalciferol is administered in combination with a cardiac relaxant.

3. The method according to claim 2, wherein the cardiac relaxant comprises a beta-adrenergic receptor blocker, an anti-hypertensive agent, an antiarrythmia agent, 2,3-butanedione monoxime or combinations thereof.

4. A method according to claim 1, wherein administering the pharmaceutical composition reduces at least one of cardiac index, stroke volume, heart mass, contraction kinetics, and E/A ratio in the subject.

5. A method according to claim 1, wherein the effective amount of 1α-hydroxysitocalciferol is from about 0.5 to about 15 μg per day.

6. A method according to claim 1, wherein the pharmaceutical composition is an oral solid dosage form.

7. A method according to claim 1, wherein the pharmaceutical composition is an injectable dosage form.

8. A method according to claim 1, wherein the therapeutically effective amount is from about 0.5 to about 100 micrograms per day.

9. A method according to claim 1, wherein the pharmaceutical composition consists essentially of a therapeutically effective amount of 1αhydroxysitocalciferol and a pharmaceutically acceptable excipient.

10. A method according to claim 1, wherein the subject is diagnosed with cardiac hypertrophy or increased interstitial fibrosis.

11. The method according to claim 1, wherein the subject is a human.

12. A method for treating a subject having a cardiac remodeling condition or in risk of having a cardiac remodeling condition, the method comprising: causing 1α-hydroxysitocalciferol to bind to vitamin D receptors in the subject's cardiomyocytes, wherein the causing the 1α-hydroxysitocalciferol to bind to the vitamin D receptors tranquilizes the cardiomyocytes, and wherein the cardiac remodeling condition is hypertrophy, increased cardiac interstitial fibrosis, or a combination thereof.

13. The method according to claim 12, wherein the causing is performed by administering to the subject a pharmaceutical composition comprising a therapeutically effective amount of the 1α-hydroxysitocalciferol and a pharmaceutically acceptable excipient.

14. The method according to claim 12, wherein the subject is a human.

* * * * *